(12) United States Patent
Van Der Laan et al.

(10) Patent No.: US 8,617,868 B2
(45) Date of Patent: *Dec. 31, 2013

(54) ASPARAGINASE ENZYME VARIANTS AND USES THEREOF

(75) Inventors: Jan Metske Van Der Laan, Breda (NL); Mark Cristiaan Stor, Gouda (NL); Ilse Lange De, Hellevoetsluis (NL); Lisette Mohrmann, Bergschenhoek (NL)

(73) Assignee: DSM IP Assets B.V., Heerlen (NL)

( * ) Notice: Subject to any disclaimer, the term of this patent is extended or adjusted under 35 U.S.C. 154(b) by 358 days.

This patent is subject to a terminal disclaimer.

(21) Appl. No.: 12/596,710

(22) PCT Filed: Apr. 17, 2008

(86) PCT No.: PCT/EP2008/054692
§ 371 (c)(1),
(2), (4) Date: Oct. 20, 2009

(87) PCT Pub. No.: WO2008/128974
PCT Pub. Date: Oct. 30, 2008

(65) Prior Publication Data
US 2010/0183765 A1 Jul. 22, 2010

(30) Foreign Application Priority Data

Apr. 20, 2007 (EP) .................... 07106612
Apr. 20, 2007 (EP) .................... 07106620
Apr. 20, 2007 (EP) .................... 07106660
Apr. 20, 2007 (EP) .................... 07106662
Apr. 20, 2007 (EP) .................... 07106664

(51) Int. Cl.
*C12N 9/78* (2006.01)
*C12N 1/20* (2006.01)
*C12N 15/00* (2006.01)
*C07H 21/04* (2006.01)

(52) U.S. Cl.
USPC .................... 435/227; 435/252.3; 435/320.1; 536/23.2

(58) Field of Classification Search
USPC .................... 435/229, 252.3, 320.1; 536/23.2
See application file for complete search history.

(56) References Cited

U.S. PATENT DOCUMENTS

| | | | |
|---|---|---|---|
| 7,396,670 B2 | 7/2008 | Budolfsen et al. | |
| 7,514,113 B2 | 4/2009 | Zyzak | |
| 7,524,519 B2 | 4/2009 | Zyzak et al. | |
| 7,666,652 B2 * | 2/2010 | Matsui et al. | 435/229 |
| 8,323,948 B2 | 12/2012 | Van Der Laan et al. | |
| 2004/0058046 A1 | 3/2004 | Zyzak et al. | |
| 2004/0101607 A1 | 5/2004 | Zyzak et al. | |
| 2005/0202153 A1 | 9/2005 | Zyzak et al. | |
| 2006/0275879 A1 | 12/2006 | Lynglev et al. | |
| 2007/0042080 A1 | 2/2007 | Plomp et al. | |
| 2008/0095883 A1 | 4/2008 | Budolfsen et al. | |
| 2008/0096260 A1 | 4/2008 | Budolfsen et al. | |
| 2009/0191310 A1 | 7/2009 | Zyzak et al. | |
| 2012/0100249 A1 | 4/2012 | Laan et al. | |

FOREIGN PATENT DOCUMENTS

| | | |
|---|---|---|
| EP | 1 704 782 | 9/2006 |
| EP | 1 704 782 A1 | 9/2006 |
| WO | 2004/026043 | 4/2004 |
| WO | 2004/026043 A1 | 4/2004 |
| WO | 2004/030468 | 4/2004 |
| WO | 2004/032648 A1 | 4/2004 |
| WO | 2004030468 A2 | 4/2004 |
| WO | 2008/110513 A1 | 9/2008 |
| WO | 2008/128974 A1 | 10/2008 |
| WO | 20081128975 A1 | 10/2008 |

OTHER PUBLICATIONS

International Search Report for PCT/EP2008/054692, mailed Sep. 10 2008.
English Translation of Office Action issued in Chilean Application No. 1128-2008 dated Apr. 19, 2012.
William G.J. et al., "Directed evolution of enzymes for biocatalysis and the life sciences," Cell Mol Life Science, Dec. 2004, 61 (24): 3034-46.
Robert A. Chica et al., "Semi-rational approaches to engineering enzyme activity: combining the benefits of directed evolution and rational design," Current Opinion in Biotechnology 2005; 16(4): 378-384.
S. Sen eta l., "Developments in Directed Evolution for Improving Enzyme Functions," Applied Biochemistry and Biotechnology, Dec. 2007; 143(3): 212-223.
Accession A1D4Y2_NEOFI Jan. 23, 2007.
European Search Report issued Jun. 25, 2010.
International Search Report for PCT/EP2008/054693, dated Sep. 3, 2008.
Accession Q4WKE2, Jul. 5, 2005.

* cited by examiner

*Primary Examiner* — Tekchand Saidha
(74) *Attorney, Agent, or Firm* — Miles & Stockbridge, P.C.

(57) ABSTRACT

The present invention relates to newly identified asparaginase polypeptide variants of SEQ ID NO: 3 and to polynucleotide sequences that encode such novel asparaginase variants. Furthermore the invention relates to the use of these novel asparaginase variants in industrial processes.

29 Claims, No Drawings

ASPARAGINASE ENZYME VARIANTS AND USES THEREOF

This application is the U.S. national phase under 35 U.S.C. 371 of International Application No. PCT/EP2008/054692, filed 17 Apr. 2008, which claims priority to EP 07106660.9, filed 20 Apr. 2007; EP 07106662.5, filed 20 Apr. 2007; EP 07106620.3, filed 20 Apr. 2007; EP 07106612.0, filed 20 Apr. 2007; and EP 07106664.1, filed 20 Apr. 2007; the entire contents of each of which are hereby incorporated by reference.

FIELD OF THE INVENTION

The invention relates to asparaginase polypeptide variants and to polynucleotide sequences comprising genes that encode these asparaginase variants. The invention features a method for identifying suitable asparaginase variants. The invention also relates to methods of using these variant proteins in industrial processes. Also included in the invention are cells transformed with a polynucleotide according to the invention suitable for producing these proteins and cells, wherein a protein according to the invention is genetically modified to enhance or reduce its activity and/or level of expression. The invention also relates to methods of using the asparaginase variants in industrial processes.

BACKGROUND OF THE INVENTION

Recently, the occurrence of acrylamide in a number of heated food products was published (Tareke et al. Chem. Res. Toxicol. 13, 517-522 (2000)). Since acrylamide is considered as probably carcinogenic for animals and humans, this finding had resulted in world-wide concern. Further research revealed that considerable amounts of acrylamide are detectable in a variety of baked, fried and oven prepared common foods and it was demonstrated that the occurrence of acrylamide in food was the result of the heating process.

A pathway for the formation of acrylamide from amino acids and reducing sugars as a result of the Maillard reaction has been proposed by Mottram et al. Nature 419:448 (2002). According to this hypothesis, acrylamide may be formed during the Maillard reaction. During baking and roasting, the Maillard reaction is mainly responsible for the color, smell and taste. A reaction associated with the Maillard is the Strecker degradation of amino acids and a pathway to acrylamide was proposed. The formation of acrylamide became detectable when the temperature exceeded 120° C., and the highest formation rate was observed at around 170° C. When asparagine and glucose were present, the highest levels of acrylamide could be observed, while glutamine and aspartic acid only resulted in trace quantities.

The official migration limit in the EU for acrylamide migrating into food from food contact plastics is set at 10 ppb (10 micrograms per kilogram). Although no official limit is yet set for acrylamide that forms during cooking, the fact that a lot of products exceed this value, especially cereals, bread products and potato or corn based products, causes concern.

Several plant raw materials are known to contain substantial levels of asparagine. In potatoes asparagine is the dominant free amino acid (940 mg/kg, corresponding with 40% of the total amino-acid content) and in wheat flour asparagine is present as a level of about 167 mg/kg, corresponding with 14% of the total free amino acids pool (Belitz and Grosch in Food Chemistry—Springer New York, 1999). The fact that acrylamide is formed mainly from asparagine (combined with reducing sugars) may explain the high levels acrylamide in fried, oven-cooked or roasted plant products. Therefore, in the interest of public health, there is an urgent need for food products that have substantially lower levels of acrylamide or, preferably, are devoid of it.

A variety of solutions to decrease the acrylamide content has been proposed, either by altering processing variables, e.g. temperature or duration of the heating step, or by chemically or enzymatically preventing the formation of acrylamide or by removing formed acrylamide.

In several patent applications the use of asparaginase for decreasing the level of asparagine and thereby the amount of acrylamide formed has been disclosed. Suitable asparaginases for this purpose have been yielded from several fungal sources, as for example *Aspergillus niger* in WO2004/030468 and *Aspergillus oryzae* in WO04/032648.

Although all L-asparaginases catalyze the same chemical conversion, this does not mean that they are suitable for the same applications. Various applications will place different demands on the conditions under which the enzymes have to operate. Physical and chemical parameters that may influence the rate of an enzymatic conversion are the temperature (which has a positive effect on the chemical reaction rates, but may have a negative effect on enzyme stability), the moisture content, the pH, the salt concentration, the structural integrity of the food matrix, the presence of activators or inhibitors of the enzyme, the concentration of the substrate and products, etc.

Therefore there exists an ongoing need for improved asparaginases for several applications having improved properties.

OBJECT OF THE INVENTION

It is an object of the invention to provide novel asparaginase variant polypeptides and polynucleotides encoding such variants. A further object is to provide recombinant strains producing such asparaginase variants. Also, a method for identifying variants is part of the invention, as well as methods of making and using the polynucleotides and polypeptides according to the invention.

SUMMARY OF THE INVENTION

The invention provides a polypeptide variant of a parent polypeptide having asparaginase activity, wherein the variant has an amino acid sequence which, when aligned with the sequence set out in SEQ ID NO: 3, comprises a substitution of an amino acid residue corresponding to any of amino acids 41, 53, 62, 63, 64, 66, 70, 71, 73, 74, 76, 77, 88, 90, 91, 101, 102, 103, 104, 106, 107, 108, 109, 111, 119, 122, 123, 132, 140, 142, 143, 145, 161, 162, 163, 164, 168, 169, 170, 195, 211, 213, 214, 215, 216, 217, 218, 219, 220, 228, 232, 233, 234, 235, 262, 267, 268, 269, 270, 271, 272, 273, 293, 295, 297, 298, 299, 300, 301, 302, 303, 304, 310, 314, 317, 318, 319, 321, 323, 324, 325, 327, 328, 329, 330, 331, 332, 333, 334, 335 or 371
said positions being defined with reference to SEQ ID NO: 3.
  The invention also provides:
  a nucleic acid sequence encoding such a variant;
  a nucleic acid construct comprising a nucleic acid sequence encoding a variant of the invention operably linked to one or more control sequences capable of directing the expression of an asparaginase in a suitable expression host;
  a recombinant expression vector comprising such a nucleic acid construct;

a recombinant host cell comprising such an expression vector;

a method for producing an asparaginase comprising cultivating such a host cell under conditions conducive to production of the asparaginase and recovering the asparaginase;

a method of producing an asparaginase polypeptide variant, which method comprises:

a) selecting a parent asparaginase polypeptide;
b) substituting at least one amino acid residue corresponding to any of
   41, 53, 62, 63, 64, 66, 70, 71, 73, 74, 76, 77, 88, 90, 91, 101, 102, 103, 104, 106, 107, 108, 109, 111, 119, 122, 123, 132, 140, 142, 143, 145, 161, 162, 163, 164, 168, 169, 170, 195, 211, 213, 214, 215, 216, 217, 218, 219, 220, 228, 232, 233, 234, 235, 262, 267, 268, 269, 270, 271, 272, 273, 293, 295, 297, 298, 299, 300, 301, 302, 303, 304, 310, 314, 317, 318, 319, 321, 323, 324, 325, 327, 328, 329, 330, 331, 332, 333, 334, 335 or 371
   said positions being defined with reference to SEQ ID NO: 3.
c) optionally substituting one or more further amino acids as defined in b);
d) preparing the variant resulting from steps a)-c);
e) determining the specific activity and/or the pH optimum of the variant; and
f) selecting a variant having an increased specific activity and/or pH optimum in comparison to the parent asparaginase polypeptide, thereby to produce an asparaginase polypeptide variant.

a composition comprising a variant of the invention or a variant obtained by a method of the invention;

use of a composition of the invention in the production of a food product; and use of a composition of the invention to reduce the amount of acrylamide formed in a thermally processed food product based on an asparagine-containing raw material.

DETAILED DESCRIPTION OF THE INVENTION

Throughout the present specification and accompanying claims, the words "comprise" and "include" and variations such as "comprises", "comprising", "includes" and "including" are to be interpreted inclusively. That is, these words are intended to convey the possible inclusion of other elements or integers not specifically recited, where the context allows.

The present invention relates to a polypeptide variant of a parent polypeptide having asparaginase activity. The variant has an amino acid sequence which, when aligned with the sequence set out in SEQ ID NO: 3, comprises a substitution of an amino acid residue corresponding to any of amino acids 41, 53, 62, 63, 64, 66, 70, 71, 73, 74, 76, 77, 88, 90, 91, 101, 102, 103, 104, 106, 107, 108, 109, 111, 119, 122, 123, 132, 140, 142, 143, 145, 161, 162, 163, 164, 168, 169, 170, 195, 211, 213, 214, 215, 216, 217, 218, 219, 220, 228, 232, 233, 234, 235, 262, 267, 268, 269, 270, 271, 272, 273, 293, 295, 297, 298, 299, 300, 301, 302, 303, 304, 310, 314, 317, 318, 319, 321, 323, 324, 325, 327, 328, 329, 330, 331, 332, 333, 334, 335 or 371
said positions being defined with reference to SEQ ID NO: 3.

That is to say, when the variant asparaginase sequence is aligned with the sequence of the asparaginase of SEQ ID NO: 3, the variant will comprise at least one substitution at a position (in the variant) corresponding to one of the positions set out above in SEQ ID NO: 3. A "substitution" in this context indicates that a position in the variant which corresponds to one of the positions set out above in SEQ ID NO: 3 comprises an amino acid residue which does not appear at that position in the parent polypeptide (which parent polypeptide may be SEQ ID NO: 3).

Those positions in a variant asparaginase polypeptide of the invention which correspond to the positions set out above in SEQ ID NO: 3 may be identified by aligning the sequence of the variant polypeptide with that of SEQ ID NO: 3 using, for example, the GAP alignment to the most homologous sequence found by the GAP program (see below for details of this program). The positions in the variant corresponding to the positions in SEQ ID NO: 3 as set out above may thus be identified and are referred to as those positions defined with reference to SEQ ID NO: 3.

The parent asparaginase polypeptide that may be used in the present invention may be any asparaginase (EC 3.5.1.1). A suitable asparaginase polypeptide may be obtained from various sources, such as for example from a plant, an animal or a microorganism. For example, an asparaginase may be obtained from *Escherichia*, *Erwinia*, *Streptomyces*, *Pseudomonas*, *Aspergillus* and *Bacillus* species. An example of a suitable *Escherichia* strain is *Escherichia coli*. An example of a suitable *Erwinia* strain is *Erwinia chrysanthemi*. Examples of suitable *Streptomyces* strains are *Streptomyces lividans* and *Streptomyces murinus*. Examples of suitable *Aspergillus* strains are *Aspergillus oryzae*, *Aspergillus nidulans* or *Aspergillus niger*. Examples of suitable *Bacillus* strains are *Bacillus alkalophilus*, *Bacillus amyloliquefaciens*, *Bacillus brevis*, *Bacillus circulans*, *Bacillus coagulans*, *Bacillus lautus*, *Bacillus lentus*, *Bacillus licheniformis*, *Bacillus megaterium*, *Bacillus stearothermophilus*, *Bacillus subtilis* or *Bacillus thurigiensis*.

An example of methods suitable for obtaining asparaginase from *Bacillus*, *Streptomyces*, *Escherichia* or *Pseudomonas* strains is described in WO 03/083043. An example of methods suitable for obtaining asparaginase from *Aspergillus* is described in WO 2004/030468 and WO 04/032468.

A preferred parent asparaginase polypeptide suitable for use in the invention is the polypeptide having the sequence set out in SEQ ID NO: 3 or having at least 80% homology with SEQ ID NO: 3, for example at least 85% homology with SEQ ID NO: 3, such as a least 85% homology with SEQ ID NO: 3, such as at least 90% homology with SEQ ID NO: 3, for example at least 95%, at least 98% or at least 99% homology with SEQ ID NO: 3.

The amino acid residues in a variant of the invention that are substituted with comparison with the sequence set out in SEQ ID NO: 3 are those which correspond to positions 41, 53, 62, 63, 64, 66, 70, 71, 73, 74, 76, 77, 88, 90, 91, 101, 102, 103, 104, 106, 107, 108, 109, 111, 119, 122, 123, 132, 140, 142, 143, 145, 161, 162, 163, 164, 168, 169, 170, 195, 211, 213, 214, 215, 216, 217, 218, 219, 220, 228, 232, 233, 234, 235, 262, 267, 268, 269, 270, 271, 272, 273, 293, 295, 297, 298, 299, 300, 301, 302, 303, 304, 310, 314, 317, 318, 319, 321, 323, 324, 325, 327, 328, 329, 330, 331, 332, 333, 334, 335 or 371
as defined in relation to the sequence of SEQ ID NO: 3.

A variant may comprises a substitution at one or more of the said positions, for example at two, three, four, at least 5, at least 10, at least 15, at least 20, at least 25, at least 30, at least 35, at least 40, at least 45, at least 50, at least 55, at least 60, at least 65, at least 70 or at all of the said positions.

A preferred subset of positions for substitution is defined by those at positions
41, 53, 62, 63, 64, 66, 70, 71, 73, 74, 76, 77, 88, 90, 91, 101, 102, 103, 104, 106, 107, 108, 109, 111, 119, 122, 123, 132, 140, 142, 143, 145, 161, 162, 163, 164, 168, 169, 170, 195, 211, 214, 215, 216, 218, 220, 228, 232, 233, 262, 267, 293, 295, 297, 298, 299, 300, 301, 303, 304, 310, 314, 317, 319, 321, 324, 330, 332, 333, 334 or 371.
as defined in relation to the sequence of SEQ ID NO: 3.

A variant may comprises a substitution at one or more of the said positions, for example at two, three, four, at least 5, at least 10, at least 15, at least 20, at least 25, at least 30, at least 35, at least 40, at least 45 or at all of the said positions.

A more preferred subset of positions for substitution is defined by those at positions
41, 53, 63, 64, 66, 73, 74, 76, 77, 88, 90, 91, 101, 106, 111, 119, 122, 123, 132, 140, 145, 161, 170, 195, 211, 218, 228, 232, 233, 262, 267, 293, 295, 297, 299, 300, 301, 303, 304, 310, 314, 317, 321, 324, 330, 332, 333 or 371,
as defined in relation to the sequence of SEQ ID NO: 3.
A even more preferred subset of positions for substitution is defined by those at positions
53, 63, 64, 66, 73, 74, 76, 77, 88, 101, 140, 170, 293,
as defined in relation to the sequence of SEQ ID NO: 3.

A variant may comprises a substitution at one or more of the said positions, for example at two, three, four, at least 5, at least 10, at least 15, at least 20 or at all of the said positions.

A variant of the invention comprises one or more substitutions as defined above. A "substitution" in this context indicates that a position in the variant which corresponds to one of the positions set out above in SEQ ID NO: 3 comprises an amino acid residue which does not appear at that position in the parent polypeptide (the parent may be SEQ ID NO: 3).

Preferred substitutions are set out in the following Table (with the positions being defined in relation to the sequence set out in SEQ ID NO: 3).

| Position | Most preferred | More preferred | Preferred |
|---|---|---|---|
| 41 | I | | IN |
| 53 | Y | | LY |
| 62 | | GAT | GATFK |
| 63 | GVS | GASV | GASIVE |
| 64 | P | | ANDP |
| 66 | P | | NKP |
| 70 | | AS | |
| 71 | | N | ASNE |
| 73 | K | QNKE | HSNDQERK |
| 74 | A | | AV |
| 76 | T | STV | STVQNKE |
| 77 | I | IL | |
| 88 | YP | YPE | |
| 90 | V | | VYF |
| 91 | E | | SNE |
| 101 | V | | VSTDH |
| 102 | S | | SRK |
| 103 | | I | LIFMT |
| 104 | | ND | AND |
| 106 | P | PQ | GAKESTNPQ |
| 107 | | N | SNE |
| 108 | | VM | VML |
| 109 | | NS | RDGNS |
| 111 | G | GS | GSTH |
| 119 | N | TN | TNMQER |
| 122 | H | EH | ADEHK |
| 123 | A | | ALT |
| 132 | S | | |
| 140 | N | | |
| 142 | | M | |
| 143 | | D | DSAG |
| 145 | S | S | |
| 161 | L | VL | VLFM |
| 162 | | T | AT |
| 163 | | A | |
| 164 | | S | GS |
| 168 | | A | AGT |
| 169 | | S | AGS |
| 170 | T | ST | EGST |
| 195 | D | | |
| 211 | S | SV | SVMINQ |
| 213 | | S | SIM |
| 214 | | H | SH |
| 215 | | ST | |
| 216 | | ST | STVLF |
| 217 | | SN | ASNDK |
| 218 | V | VLT | |
| 219 | | NQE | ASNQE |
| 220 | | AS | |
| 228 | H | NH | ASNH |
| 232 | V | VI | VIF |
| 233 | V | VH | VHLREYFS |
| 234 | | ND | GND |
| 235 | | GS | GSDI |
| 262 | CH | | |
| 267 | Y | Y | |
| 268 | | NAG | GANTF |
| 269 | | HF | |
| 270 | | Q | ASIQ |
| 271 | | N | NE |
| 272 | | A | AIDQ |
| 273 | | QTS | QTSPDE |
| 293 | SV | SVET | SVETML |
| 295 | S | NS | |
| 297 | S | NSTA | |
| 298 | | ILM | ILMWFT |
| 299 | S | SDA | SDAPHYN |
| 300 | I | SI | EDHKANQIS |
| 301 | P | TPAGD | GATPNRDEYK |
| 302 | | Y | QNHWVIY |
| 303 | S | YFS | GLKEDIAYFS |
| 304 | T | ATSD | ATSDNKP |
| 310 | V | ATV | AVMT |
| 314 | D | SND | GASNDQH |
| 317 | I | I | |
| 318 | | MIA | |
| 319 | | ATLR | ATLRVIYH |
| 321 | T | ST | STHRKA |
| 323 | | VS | IVS |
| 324 | G | GP | MAGP |
| 325 | | AST | ASTDEW |
| 327 | | M | MIPYSARVT |
| 328 | | ST | STI |
| 329 | | AT | ATLG |
| 330 | S | PSYTIL | DERQVPSYTIL |
| 331 | | AT | ATGNDEKR |
| 332 | A | A | ANSGEKPQ |
| 333 | E | EDS | EDSIFAGK |
| 334 | | GTDE | GTDEPVI |
| 335 | | TGD | |
| 371 | M | | AIM |

A variant according to the invention may have an amino acid sequence which, when aligned with the sequence set out in SEQ ID NO: 3, comprises one or more of Ile at position 41, Tyr at position 53, Gly or Val or Ser at position 63, Pro at position 64, Pro at position 66, Lys at position 73, Ala at position 74, Thr at position 76, Ile at position 77, Tyr or Pro at position 88, Val at position 90, Glu at position 91, Val at position 101, Pro at position 106, Gly at position 111, Asn at position 119, His at position 122, Ala at position 123, Ser at position 132, Asn at position 140, Ser at position 145, Leu at position 161, Thr at position 170, Asp at position 195, Ser at position 211, Val at position 218, His at position 228, Val at position 232, Val at position 233, Cys or His at position 262, Tyr at position 267, Ser or Val at position 293, Ser at position 295, Ser at position 297, Ser at position 299, Ile at position 300, Pro at position 301, Ser at position 303, Thr at position 304, Val at position 310, Asp at position 314, Ile at position 317, Thr at position 321, Gly at position 324, Ser at position 330, Ala at position 332, Glu at position 333 or Met at position 371
said positions being defined with reference to SEQ ID NO: 3.

In a preferred embodiment a variant according to the invention may have an amino acid sequence which, when aligned with the sequence set out in SEQ ID NO: 3, comprises one or more of
Tyr at position 53, Gly or Val at position 63, Pro at position 64, Pro at position 66, Lys at position 73, Ala at position 74, Thr at position 76, Ile at position 77, Tyr or Pro at position 88, Val at position 101, Asn at position 140, Thr at position 170, Ser or Val at position 293,
said positions being defined with reference to SEQ ID NO: 3.

In a preferred embodiment a variant according to the invention may have an amino acid sequence which, when aligned with the sequence set out in SEQ ID NO: 3, comprises at least one substitution of an amino acid residue corresponding to amino acid 63, preferably comprising a Gly or Val at position 63, said positions being defined with reference to SEQ ID NO: 3 and wherein the parent polypeptide of said variant preferably corresponds to SEQ ID NO: 3.

Examples of a variant of a parent polypeptide having asparaginase activity, wherein the variant has an amino acid sequence which, when aligned with the sequence set out in SEQ ID NO: 3, comprises at least one substitution of an amino acid residue corresponding to amino acid 63, said positions being defined with reference to SEQ ID NO: 3. and wherein the parent polypeptide corresponds to SEQ ID NO: 3, are the polypeptide comprising the substitutions D63G and G132S (tentatively called ASN01), the polypeptide comprising the substitutions D63G, D111G and R122H (tentatively called ASN02), the polypeptide comprising the substitutions D63V and T300I (tentatively called ASN03).

In another embodiment a variant according to the invention may have an amino acid sequence which, when aligned with the sequence set out in SEQ ID NO: 3, comprises at least one substitution of an amino acid residue corresponding to amino acid 64, preferably comprising a Pro at position 64, said positions being defined with reference to SEQ ID NO: 3 and wherein the parent polypeptide of said variant preferably corresponds to SEQ ID NO: 3.

Examples of a variant of a parent polypeptide having asparaginase activity, wherein the variant has an amino acid sequence which, when aligned with the sequence set out in SEQ ID NO: 3, comprises at least one substitution of an amino acid residue corresponding to amino acid 64, said positions being defined with reference to SEQ ID NO: 3. and wherein the parent polypeptide corresponds to SEQ ID NO: 3, is the polypeptide comprising the substitutions S64P and I310V (tentatively called ASN04).

In yet another embodiment a variant according to the invention may have an amino acid sequence which, when aligned with the sequence set out in SEQ ID NO: 3, comprises at least one substitution of an amino acid residue corresponding to amino acid 66, preferably comprising a Pro at position 66, said positions being defined with reference to SEQ ID NO: 3 and wherein the parent polypeptide of said variant preferably corresponds to SEQ ID NO: 3.

Examples of a variant of a parent polypeptide having asparaginase activity, wherein the variant has an amino acid sequence which, when aligned with the sequence set out in SEQ ID NO: 3, comprises at least one substitution of an amino acid residue corresponding to amino acid 66, said positions being defined with reference to SEQ ID NO: 3. and wherein the parent polypeptide corresponds to SEQ ID NO: 3, is the polypeptide comprising the substitutions T41I, S66P and V371M (tentatively called ASN05).

In yet another embodiment a variant according to the invention may have an amino acid sequence which, when aligned with the sequence set out in SEQ ID NO: 3, comprises at least one substitution of an amino acid residue corresponding
to amino acid 73, 74, 293,
preferably comprising one or more of Lys at position 73, Ala at position 74, Ser or Val at position 293
said positions being defined with reference to SEQ ID NO: 3 and wherein the parent polypeptide of said variant preferably corresponds to SEQ ID NO: 3.

Examples of a variant of a parent polypeptide having asparaginase activity, wherein the variant has an amino acid sequence which, when aligned with the sequence set out in SEQ ID NO: 3, comprises at least one substitution of an amino acid residue corresponding to amino acid 73, 74 or 293, said positions being defined with reference to SEQ ID NO: 3. and wherein the parent polypeptide corresponds to SEQ ID NO: 3, are the polypeptide comprising the substitutions G195D and A293V (tentatively called ASN14), the polypeptide comprising the substitutions T73K; S74A; and A293S (tentatively called ASN15) or the polypeptide comprising the substitutions T73K, S74A, E106P, A293S, G297S, T299S, Q319A, M321T, and V324G (tentatively called ASN16).

In a further embodiment a variant according to the invention may have an amino acid sequence which, when aligned with the sequence set out in SEQ ID NO: 3, comprises at least one substitution of an amino acid residue corresponding
to amino acid 76 or 101
preferably comprising one or more of Thr at position 76, or Val at position 101
said positions being defined with reference to SEQ ID NO: 3 and wherein the parent polypeptide of said variant preferably corresponds to SEQ ID NO: 3.

Examples of a variant of a parent polypeptide having asparaginase activity, wherein the variant has an amino acid sequence which, when aligned with the sequence set out in SEQ ID NO: 3, comprises at least one substitution of an amino acid residue corresponding to amino acid 76 or 101, said positions being defined with reference to SEQ ID NO: 3. and wherein the parent polypeptide corresponds to SEQ ID NO: 3, is the polypeptide comprising the substitutions A76T and A101V (tentatively called ASN06).

In yet a further embodiment a variant according to the invention may have an amino acid sequence which, when aligned with the sequence set out in SEQ ID NO: 3, comprises at least one substitution of an amino acid residue corresponding
to amino acid 77, preferably comprising a Ile at position 77
said positions being defined with reference to SEQ ID NO: 3 and wherein the parent polypeptide of said variant preferably corresponds to SEQ ID NO: 3.

Examples of a variant of a parent polypeptide having asparaginase activity, wherein the variant has an amino acid sequence which, when aligned with the sequence set out in SEQ ID NO: 3, comprises at least one substitution of an amino acid residue corresponding to amino acid 77, said positions being defined with reference to SEQ ID NO: 3. and wherein the parent polypeptide corresponds to SEQ ID NO: 3, is the polypeptide comprising the substitutions V77I, V123A and E314D (tentatively called ASN07).

In an embodiment a variant according to the invention may have an amino acid sequence which, when aligned with the sequence set out in SEQ ID NO: 3, comprises at least one substitution of an amino acid residue corresponding to amino acid 88, preferably comprising a Tyr or Pro at position 88 said positions being defined with reference to SEQ ID NO: 3 and wherein the parent polypeptide of said variant preferably corresponds to SEQ ID NO: 3.

Examples of a variant of a parent polypeptide having asparaginase activity, wherein the variant has an amino acid sequence which, when aligned with the sequence set out in SEQ ID NO: 3, comprises at least one substitution of an amino acid residue corresponding to amino acid 88, said positions being defined with reference to SEQ ID NO: 3. and wherein the parent polypeptide corresponds to SEQ ID NO: 3, is the polypeptide comprising the substitution S88Y (tentatively called ASN08) or the polypeptide comprising the substitutions S88P, I161L and R262C (tentatively called ASN09).

In another embodiment a variant according to the invention may have an amino acid sequence which, when aligned with the sequence set out in SEQ ID NO: 3, comprises at least one substitution of an amino acid residue corresponding to amino acid 140, preferably comprising a Asn at position 140 said positions being defined with reference to SEQ ID NO: 3 and wherein the parent polypeptide of said variant preferably corresponds to SEQ ID NO: 3.

Examples of a variant of a parent polypeptide having asparaginase activity, wherein the variant has an amino acid sequence which, when aligned with the sequence set out in SEQ ID NO: 3, comprises at least one substitution of an amino acid residue corresponding to amino acid 140, said positions being defined with reference to SEQ ID NO: 3. and wherein the parent polypeptide corresponds to SEQ ID NO: 3, is the polypeptide comprising the substitution D140N (tentatively called ASN10).

In one embodiment a variant according to the invention may have an amino acid sequence which, when aligned with the sequence set out in SEQ ID NO: 3, comprises at least one substitution of an amino acid residue corresponding to amino acid 170, preferably comprising a Thr at position 170 said positions being defined with reference to SEQ ID NO: 3 and wherein the parent polypeptide of said variant preferably corresponds to SEQ ID NO: 3.

Examples of a variant of a parent polypeptide having asparaginase activity, wherein the variant has an amino acid sequence which, when aligned with the sequence set out in SEQ ID NO: 3, comprises at least one substitution of an amino acid residue corresponding to amino acid 170, said positions being defined with reference to SEQ ID NO: 3. and wherein the parent polypeptide corresponds to SEQ ID NO: 3, is the polypeptide comprising the substitutions D91E, A170T and R262H (tentatively called ASN11).

In one more embodiment a variant according to the invention may have an amino acid sequence which, when aligned with the sequence set out in SEQ ID NO: 3, comprises at least one substitution of an amino acid residue corresponding to amino acid 53, preferably comprising a Tyr at position 53 said positions being defined with reference to SEQ ID NO: 3 and wherein the parent polypeptide of said variant preferably corresponds to SEQ ID NO: 3.

Examples of a variant of a parent polypeptide having asparaginase activity, wherein the variant has an amino acid sequence which, when aligned with the sequence set out in SEQ ID NO: 3, comprises at least one substitution of an amino acid residue corresponding to amino acid 53, said positions being defined with reference to SEQ ID NO: 3. and wherein the parent polypeptide corresponds to SEQ ID NO: 3, is the polypeptide comprising the substitutions F53Y and K119N (tentatively called ASN13).

A further examples of a variant of a parent polypeptide having asparaginase activity, wherein the variant has an amino acid sequence which, when aligned with the sequence set out in SEQ ID NO: 3, comprises at least one substitution of an amino acid residue corresponding to any of amino acids 41, 53, 63, 64, 66, 73, 74, 76, 77, 88, 90, 91, 101, 106, 111, 119, 122, 123, 132, 140, 145, 161, 170, 195, 211, 218, 228, 232, 233, 262, 267, 293, 295, 297, 299, 300, 301, 303, 304, 310, 314, 317, 321, 324, 330, 332, 333 or 371 said positions being defined with reference to SEQ ID NO: 3. and wherein the parent polypeptide corresponds to SEQ ID NO: 3, is the polypeptide comprising the substitutions L90V, K119N, Y228H, and R262C (tentatively called ASN12).

A variant of the invention may also comprise additional modifications in comparison to the parent at positions other than those specified above, for example, one or more additional substitutions, additions or deletions. A variant of the invention may comprise a combination of different types of modification of this sort. A variant may comprise one, two, three, four, least 5, at least 10, at least 15, at least 20, at least 25, at least 30 or more such modifications (which may all be of the same type or may be different types of modification). Typically, the additional modifications may be substitutions.

A variant according to the invention may have at least 80% homology with the parent asparaginase polypeptide, for example at least 85% homology with the parent polypeptide, such as 90% homology with the parent polypeptide, at least 95% homology with the parent polypeptide, at least 98% homology with the parent polypeptide or at least 99% homology with the parent polypeptide.

A variant of the invention will typically retain asparaginase activity (EC 3.5.1.1). That is to say, a variant of the invention will typically be capable of catalysing the hydrolysis of asparagine to aspartic acid. A variant of the invention is, therefore, one which is typically capable of modifying the side chains of asparaginase that are involved in the formation of acrylamide during the production of a food product involving at least one heating step.

Preferably, a variant of the invention will typically exhibit improved properties in comparison with the parent asparaginase polypeptide from which it is derived. Such an improved property will typically be one which is relevant if the variant were to be used as set out below, for example in a method for preparing a foodstuff.

Such properties include, but are not limited to, increased specific activity (such that it may be possible to use a smaller amount of the variant in a method for the preparation of a foodstuff as compared to the amount of parent asparaginase required), an increased or decreased pH optimum, more particularly a pH optimum more suited for use in a method for the preparation of a foodstuff (as compared to the parent asparaginase) and increased thermostability.

In one embodiment a variant protein according to the invention may have a pH optimum which is higher than that of the parent polypeptide or lower than the parent polypeptide. Preferably the pH optimum of the variant protein is higher than that of the parent polypeptide. Preferably the parent polypeptide is that according to SEQ ID NO: 3. For example, the wild-type asparaginase from *A. niger* (as disclosed in SEQ ID NO: 3) has a pH optimum of from pH 4 to pH 5. A variant protein of the invention may be more alkaliphilic than such a wild-type enzyme, i.e. may, for example, have a pH optimum of from pH 5 to pH 8, preferably from pH 6 to pH 7. Optionally a variant protein of the invention may be more acidophilic than the wild type asparaginase.

Preferably a variant asparaginase protein according to the invention may have a pH, which is higher than the pH optimum and at which 50% of the asparaginase activity is still present, (hereafter indicated as alkaline pH), which is higher than that of the parent asparaginase. When the parent asparaginase is that according to SEQ ID NO: 3 the variant protein may have an alkaline pH at which 50% of the activity is observed which is at least 6.9, preferably, at least 7.0, at least 7.5, preferably at least 8.

A variant which exhibits a property which is improved in relation to the parent asparaginase is one which demonstrates a measurable reduction or increase in the relevant property, typically such that the variant is more suited to use as set out below, for example in a method for the production of a foodstuff.

Preferably a variant protein according to the invention may have a specific activity which is higher than that of the parent polypeptide measured at the same pH. With specific activity of a variant protein it is herewith intended the asparaginase activity of the variant protein measured in units/mg of pure protein. Preferably the specific activity of the variant protein according to the invention is higher at least one pH, preferably a pH between 4 and 8, than that of the parent polypeptide measured at the same pH.

In another embodiment of the invention the variant asparaginase is more thermophilic than the parent asparaginase polypeptide.

The property may thus be decreased by at least 10%, at least 20%, at least 30%, at least 40% at least 50%, at least 60%, at least 70%, at least 80%, at least 90%, at least 95% or at least 99%. Alternatively, the property may be increased by at least 10%, at least 25%, at least 50%, at least 100%, at least, 200%, at least 500% or at least 1000%. The percentage decrease or increase in this context represents the percentage decrease or increase in comparison to the parent asparaginase polypeptide. It is well known to the skilled person how such percentage changes may be measured—it is a comparison of the activity of the parent asparaginase and the variant asparaginase.

The variants described herein are collectively comprised in the terms "a polypeptide according to the invention" or "a variant according to the invention".

The terms "peptide" and "oligopeptide" are considered synonymous (as is commonly recognized) and each term can be used interchangeably as the context requires to indicate a chain of at least two amino acids coupled by peptidyl linkages. The word "polypeptide" is used herein for chains containing more than seven amino acid residues. All oligopeptide and polypeptide formulas or sequences herein are written from left to right and in the direction from amino terminus to carboxy terminus. The one-letter code of amino acids used herein is commonly known in the art and can be found in Sambrook, et al. (Molecular Cloning: A Laboratory Manual, 2nd, ed. Cold Spring Harbor Laboratory, Cold Spring Harbor Laboratory Press, Cold Spring Harbor, N.Y., 1989).

By "isolated" polypeptide or protein is intended a polypeptide or protein removed from its native environment. For example, recombinantly produced polypeptides and proteins expressed in host cells are considered isolated for the purpose of the invention as are recombinant polypeptides which have been substantially purified by any suitable technique such as, for example, the single-step purification method disclosed in Smith and Johnson, Gene 67:31-40 (1988).

A polypeptide variant according to the invention can be recovered and purified from recombinant cell cultures by methods known in the art. Most preferably, high performance liquid chromatography ("HPLC") is employed for purification.

Polypeptides of the present invention include products of chemical synthetic procedures, and products produced by recombinant techniques from a prokaryotic or eukaryotic host, including, for example, bacterial, yeast, higher plant, insect and mammalian cells. Depending upon the host employed in a recombinant production procedure, the polypeptides of the present invention may be glycosylated or may be non-glycosylated. In addition, polypeptides of the invention may also include an initial modified methionine residue, in some cases as a result of host-mediated processes.

The invention also features biologically active fragments of the polypeptide variants according to the invention. Such fragments are considered to be encompassed within the term "a variant of the invention".

Biologically active fragments of a polypeptide variant of the invention include polypeptides comprising amino acid sequences sufficiently identical to or derived from the amino acid sequence of a variant protein of the invention which include fewer amino acids than the full length protein but which exhibit at least one biological activity of the corresponding full-length protein. Typically, biologically active fragments comprise a domain or motif with at least one activity of a variant protein of the invention. A biologically active fragment of a protein of the invention can be a polypeptide which is, for example, 10, 25, 50, 100 or more amino acids in length. Moreover, other biologically active portions, in which other regions of the protein are deleted, can be prepared by recombinant techniques and evaluated for one or more of the biological activities of the native form of a polypeptide of the invention.

Typically, a protein fragment of the invention will comprise one or more of the substitutions defined herein.

The invention also features nucleic acid fragments which encode the above biologically active fragments (which biologically active fragments are themselves variants of the invention).

As set out above, the present invention provides polynucleotides encoding the variant polypeptides of the invention. The invention also relates to an isolated polynucleotide encoding at least one functional domain of a polypeptide variant of the invention. Typically, such a domain will comprise one or more of the substitutions described herein.

In one embodiment of the invention, the nucleic acid sequence according to the invention encodes a polypeptide, wherein the polypeptide is a variant comprising an amino acid sequence that has one or more truncation(s), and/or at least one substitution, deletion and/or insertion of an amino acid as compared to the parent asparaginase. Such a polypeptide will, however, typically comprise one or more of the substitutions described herein.

As used herein, the terms "gene" and "recombinant gene" refer to nucleic acid molecules which include an open reading frame encoding a variant as described herein. A gene may include coding sequences, non-coding sequences, introns and regulatory sequences. That is to say, a "gene", as used herein, may refer to an isolated nucleic acid molecule as defined herein. Accordingly, the term "gene", in the context of the present application, does not refer only to naturally-occurring sequences.

A nucleic acid molecule of the present invention can be generated using standard molecular biology techniques well known to those skilled in the art taken in combination with the sequence information provided herein.

For example, using standard synthetic techniques, the required nucleic acid molecule may be synthesized de novo. Such a synthetic process will typically be an automated process.

Alternatively, a nucleic acid molecule of the invention may be generated by use of site-directed mutagenesis of an existing nucleic acid molecule, for example a wild-type nucleic acid molecule. Site-directed mutagenesis may be carried out using a number of techniques well know to those skilled in the art.

In one such method, mentioned here merely by way of example, PCR is carried out on a plasmid template using oligonucleotide "primers" encoding the desired substitution. As the primers are the ends of newly-synthesized strands, should there be a mis-match during the first cycle in binding the template DNA strand, after that first round, the primer-based strand (containing the mutation) would be at equal concentration to the original template. After successive cycles, it would exponentially grow, and after 25, would outnumber the original, unmutated strand in the region of 8 million: 1, resulting in a nearly homogeneous solution of mutated amplified fragments. The template DNA may then be eliminated by enzymatic digestion with, for example using a restriction enzyme which cleaves only methylated DNA, such as Dpn1. The template, which is derived from an alkaline lysis plasmid preparation and therefore is methylated, is destroyed in this step, but the mutated plasmid is preserved because it was generated in vitro and is unmethylated as a result.

In such a method more than one mutation (encoding a substitution as described herein) may be introduced into a nucleic acid molecule in a single PCR reaction, for example by using one or more oligonucleotides, each comprising one or more mis-matches. Alternatively, more than one mutation may be introduced into a nucleic acid molecule by carrying out more than one PCR reaction, each reaction introducing one or more mutations, so that altered nucleic acids are introduced into the nucleic acid in a sequential, iterative fashion.

A nucleic acid of the invention can be generated using cDNA, mRNA or alternatively, genomic DNA, as a template and appropriate mis-matched oligonucleotide primers according to the site-directed mutagenesis technique described above. A nucleic acid molecule derived in this way can be cloned into an appropriate vector and characterized by DNA sequence analysis.

A nucleic acid sequence of the invention may comprise one or more deletions, i.e. gaps, in comparison to the parent asparaginase. Such deletions/gaps may also be generated using site-directed mutagenesis using appropriate oligonucleotides. Techniques for generating such deletions are well known to those skilled in the art.

Furthermore, oligonucleotides corresponding to or hybridizable to nucleotide sequences according to the invention can be prepared by standard synthetic techniques, e.g., using an automated DNA synthesizer.

Also, complementary nucleic acid molecules are included in the present invention. A nucleic acid molecule which is complementary to another nucleotide sequence is one which is sufficiently complementary to the other nucleotide sequence such that it can hybridize to the other nucleotide sequence thereby forming a stable duplex.

One aspect of the invention pertains to isolated nucleic acid molecules that encode a variant of the invention, or a biologically active fragment or domain thereof, as well as nucleic acid molecules sufficient for use as hybridization probes to identify nucleic acid molecules encoding a polypeptide of the invention and fragments of such nucleic acid molecules suitable for use as PCR primers for the amplification or mutation of nucleic acid molecules, such as for the preparation of nucleic acid molecules of the invention.

An "isolated polynucleotide" or "isolated nucleic acid" is a DNA or RNA that is not immediately contiguous with both of the coding sequences with which it is immediately contiguous (one on the 5' end and one on the 3' end) in the naturally occurring genome of the organism from which it is derived. Thus, in one embodiment, an isolated nucleic acid includes some or all of the 5' non-coding (e.g., promotor) sequences that are immediately contiguous to the coding sequence. The term therefore includes, for example, a recombinant DNA that is incorporated into a vector, into an autonomously replicating plasmid or virus, or into the genomic DNA of a prokaryote or eukaryote, or which exists as a separate molecule (e.g., a cDNA or a genomic DNA fragment produced by PCR or restriction endonuclease treatment) independent of other sequences. It also includes a recombinant DNA that is part of a hybrid gene encoding an additional polypeptide that is substantially free of cellular material, viral material, or culture medium (when produced by recombinant DNA techniques), or chemical precursors or other chemicals (when chemically synthesized). Moreover, an "isolated nucleic acid fragment" is a nucleic acid fragment that is not naturally occurring as a fragment and would not be found in the natural state.

As used herein, the terms "polynucleotide" or "nucleic acid molecule" are intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA. The nucleic acid may be synthesized using oligonucleotide analogs or derivatives (e.g., inosine or phosphorothioate nucleotides). Such oligonucleotides can be used, for example, to prepare nucleic acids that have altered base-pairing abilities or increased resistance to nucleases.

Another embodiment of the invention provides an isolated nucleic acid molecule which is antisense to a nucleic acid molecule of the invention.

The terms "homology" or "percent identity" are used interchangeably herein. For the purpose of this invention, it is defined here that in order to determine the percent identity of two amino acid sequences or two nucleic acid sequences, the sequences are aligned for optimal comparison purposes (e.g., gaps can be introduced in the sequence of a first amino acid or nucleic acid for optimal alignment with a second amino or nucleic acid sequence). The amino acid or nucleotide residues at corresponding amino acid or nucleotide positions are then compared. When a position in the first sequence is occupied by the same amino acid or nucleotide residue as the corresponding position in the second sequence, then the molecules are identical at that position. The percent identity between the two sequences is a function of the number of identical positions shared by the sequences (i.e., % identity=number of identical positions/total number of positions (i.e. overlapping positions)×100). Preferably, the two sequences are the same length.

A sequence comparison may be carried out over the entire lengths of the two sequences being compared or over fragment of the two sequences. Typically, the comparison will be carried out over the full length of the two sequences being compared. However, sequence identity may be carried out over a region of, for example, twenty, fifty, one hundred or more contiguous amino acid residues.

The skilled person will be aware of the fact that several different computer programs are available to determine the homology between two sequences. For instance, a comparison of sequences and determination of percent identity between two sequences can be accomplished using a mathematical algorithm. In a preferred embodiment, the percent identity between two amino acid or nucleic acid sequences is determined using the Needleman and Wunsch (J. Mol. Biol. (48): 444-453 (1970)) algorithm which has been incorporated into the GAP program in the Accelrys GCG software package (available at http://www.accelrys.com/products/gcg/), using either a Blosum 62 matrix or a PAM250 matrix, and a gap weight of 16, 14, 12, 10, 8, 6, or 4 and a length weight of 1, 2, 3, 4, 5, or 6. The skilled person will appreciate that all these different parameters will yield slightly different results but that the overall percentage identity of two sequences is not significantly altered when using different algorithms.

The protein sequences or nucleic acid sequences of the present invention can further be used as a "query sequence" to perform a search against public databases to, for example, identify other family members or related sequences. Such searches can be performed using the BLASTN and BLASTP programs (version 2.0) of Altschul, et al. (1990) J. Mol. Biol. 215:403-10. BLAST protein searches can be performed with the BLASTP program, score=50, wordlength=3 to obtain amino acid sequences homologous to protein molecules of the invention. To obtain gapped alignments for comparison purposes, Gapped BLAST can be utilized as described in Altschul et al., (1997) Nucleic Acids Res. 25(17): 3389-3402. When utilizing BLAST and Gapped BLAST programs, the default parameters of the respective programs (e.g., BLASTP and BLASTN) can be used. See the homepage of the National Center for Biotechnology Information at http://www.ncbi.nlm.nih.gov/.

Another aspect of the invention pertains to vectors, preferably expression vectors, containing a nucleic acid encoding a variant asparaginase of the invention.

As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". In general, expression vectors of utility in recombinant DNA techniques are often in the form of plasmids. The terms "plasmid" and "vector" can be used interchangeably herein as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid of the invention in a form suitable for expression of the nucleic acid in a host cell, which means that the recombinant expression vector includes one or more regulatory sequences, selected on the basis of the host cells to be used for expression, which is operatively linked to the nucleic acid sequence to be expressed. Within a recombinant expression vector, "operatively linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signal). Such regulatory sequences are described, for example, in Goeddel; Gene Expression Technology: Methods in Enzymology 185, Academic Press, San Diego, Calif. (1990). Regulatory sequences include those which direct constitutive expression of a nucleotide sequence in many types of host cells and those which direct expression of the nucleotide sequence only in a certain host cell (e.g. tissue-specific regulatory sequences). It will be appreciated by those skilled in the art that the design of the expression vector can depend on such factors as the choice of the host cell to be transformed, the level of expression of protein desired, etc. The expression vectors of the invention can be introduced into host cells to thereby produce proteins or peptides, encoded by nucleic acids as described herein (e.g. the asparaginase variant of SEQ ID NO: 3 or a variant thereof, for example a functional equivalent or fragment, or a fusion protein comprising one or more of such variants).

The recombinant expression vectors of the invention can be designed for expression of variant proteins of the invention in prokaryotic or eukaryotic cells. For example, a variant protein of the invention can be expressed in bacterial cells such as E. coli, insect cells (using baculovirus expression vectors) yeast cells or mammalian cells. Suitable host cells are discussed further in Goeddel, Gene Expression Technology Methods in Enzymology 185, Academic Press, San Diego, Calif. (1990). Alternatively, the recombinant expression vector can be transcribed and translated in vitro, for example using T7 promoter regulatory sequences and T7 polymerase.

Expression vectors useful in the present invention include chromosomal-, episomal- and virus-derived vectors e.g., vectors derived from bacterial plasmids, bacteriophage, yeast episome, yeast chromosomal elements, viruses such as baculoviruses, papova viruses, vaccinia viruses, adenoviruses, fowl pox viruses, pseudorabies viruses and retroviruses, and vectors derived from combinations thereof, such as those derived from plasmid and bacteriophage genetic elements, such as cosmids and phagemids.

The DNA insert should be operatively linked to an appropriate promoter, such as the phage lambda PL promoter, the E. coli lac, trp and tac promoters, the SV40 early and late promoters and promoters of retroviral LTRs, to name a few. Other suitable promoters will be known to the skilled person. In a specific embodiment, promoters are preferred that are capable of directing a high expression level of asparaginase in filamentous fungi. Such promoters are known in the art. The expression constructs may contain sites for transcription initiation, termination, and, in the transcribed region, a ribosome binding site for translation. The coding portion of the mature transcripts expressed by the constructs will include a translation initiating AUG at the beginning and a termination codon appropriately positioned at the end of the polypeptide to be translated.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-percipitation, DEAE-dextran-mediated transfection, transduction, infection, lipofection, cationic lipidmediated transfection or electroporation. Suitable methods for transforming or transfecting host cells can be found in Sambrook, et al. (Molecular Cloning: A Laboratory Manual, 2nd, ed. Cold Spring Harbor Laboratory, Cold Spring Harbor Laboratory Press, Cold Spring Harbor, N.Y., 1989), Davis et al., Basic Methods in Molecular Biology (1986) and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Preferred selectable markers include those which confer resistance to drugs, such as G418, hygromycin and methatrexate. Nucleic acid encoding a selectable marker can be introduced into a host cell on the same vector as that encoding a variant protein of the invention or can be introduced on a separate vector. Cells stably transfected with the introduced nucleic acid can be identified by drug selection (e.g. cells that have incorporated the selectable marker gene will survive, while the other cells die).

Expression of proteins in prokaryotes is often carried out in *E. coli* with vectors containing constitutive or inducible promoters directing the expression of either fusion or non-fusion proteins. Fusion vectors add a number of amino acids to a protein encoded therein, e.g. to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein.

As indicated, the expression vectors will preferably contain selectable markers. Such markers include dihydrofolate reductase or neomycin resistance for eukaryotic cell culture and tetracyline or ampicillin resistance for culturing in *E. coli* and other bacteria. Representative examples of appropriate host include bacterial cells, such as *E. coli, Streptomyces Salmonella typhimurium* and certain *Bacillus* species; fungal cells such as *Aspergillus* species, for example *A. niger, A. oryzae* and *A. nidulans*, such as yeast such as *Kluyveromyces*, for example *K. lactis* and/or *Puchia*, for example *P. pastoris*; insect cells such as *Drosophila* S2 and *Spodoptera* Sf9; animal cells such as CHO, COS and Bowes melanoma; and plant cells. Appropriate culture mediums and conditions for the above-described host cells are known in the art.

Vectors preferred for use in bacteria are for example disclosed in WO-A1-2004/074468, which are hereby enclosed by reference. Other suitable vectors will be readily apparent to the skilled artisan.

Known bacterial promotors suitable for use in the present invention include the promoters disclosed in WO-A1-2004/074468, which are hereby incorporated by reference.

Transcription of the DNA encoding a variant of the present invention by higher eukaryotes may be increased by inserting an enhancer sequence into the vector. Enhancers are cis-acting elements of DNA, usually about from 10 to 300 bp that act to increase transcriptional activity of a promoter in a given host cell-type. Examples of enhancers include the SV40 enhancer, which is located on the late side of the replication origin at by 100 to 270, the cytomegalovirus early promoter enhancer, the polyoma enhancer on the late side of the replication origin, and adenovirus enhancers.

For secretion of the translated protein into the lumen of the endoplasmic reticulum, into the periplasmic space or into the extracellular environment, appropriate secretation signal may be incorporated into the expressed polypeptide. The signals may be endogenous to the polypeptide or they may be heterologous signals.

A variant of the invention may be expressed in form such that it may include additional heterologous functional regions, for example secretion signals. A variant of the invention may also comprise, for example, a region of additional amino acids, particularly charged amino acids, added to the N-terminus of the polypeptide for instance to improve stability and persistence in the host cell, during purification or during subsequent handling and storage. Also, peptide moieties may be added to a variant of the invention to facilitate purification, for example by the addition of histidine residues or a T7 tag.

The variants of the invention, such as proteins of the present invention or functional equivalents thereof, e.g., biologically active portions and fragments thereof, can be operatively linked to a non-variant polypeptide (e.g., heterologous amino acid sequences) to form fusion proteins. A "non-variant polypeptide" in this context refers to a polypeptide having an amino acid sequence corresponding to a protein which is not substantially homologous to a variant asparaginase of the invention.

Within a fusion protein, the variant of the invention can correspond to a full length sequence or a biologically active fragment of a polypeptide of the invention. In a preferred embodiment, a fusion protein of the invention comprises at least two biologically active portions. Within the fusion protein, the term "operatively linked" is intended to indicate that the variant polypeptide and the non-variant polypeptide are fused in-frame to each other. The non-variant polypeptide can be fused to the N-terminus or C-terminus of the variant polypeptide.

For example, in one embodiment, the fusion protein is a fusion protein in which the variant sequence/s is/are fused to the C-terminus of the GST sequences. Such fusion proteins can facilitate the purification of a recombinant variant according to the invention. In another embodiment, the fusion protein is a variant of the invention containing a heterologous signal sequence at its N-terminus. In certain host cells (e.g., mammalian and yeast host cells), expression and/or secretion of a variant of the invention can be increased through use of a hetereologous signal sequence.

In another example, the gp67 secretory sequence of the baculovirus envelope protein can be used as a heterologous signal sequence (Current Protocols in Molecular Biology, Ausubel et al., eds., John Wiley & Sons, 1992). Other examples of eukaryotic heterologous signal sequences include the secretory sequences of melittin and human placental alkaline phosphatase (Stratagene; La Jolla, Calif.). In yet another example, useful prokarytic heterologous signal sequences include the phoA secretory signal (Sambrook et al., supra) and the protein A secretory signal (Pharmacia Biotech; Piscataway, N.J.).

A signal sequence can be used to facilitate secretion and isolation of a variant of the invention. Signal sequences are typically characterized by a core of hydrophobic amino acids, which are generally cleaved from the mature protein during secretion in one or more cleavage events. Such signal peptides contain processing sites that allow cleavage of the signal sequence from the mature proteins as they pass through the secretory pathway. The signal sequence may direct secretion of the variant, such as from a eukaryotic host into which the expression vector is transformed, and the signal sequence may then be subsequently or concurrently cleaved. The variant of the invention may then be readily purified from the extracellular medium by known methods. Alternatively, the signal sequence can be linked to the variant of interest using a sequence, which facilitates purification, such as with a GST domain. Thus, for instance, the sequence encoding the variant of the invention may be fused to a marker sequence, such as a sequence encoding a peptide, which facilitates purification of the fused variant of the invention. In certain preferred embodiments of this aspect of the invention, the marker sequence is a hexa-histidine peptide, such as the tag provided in a pQE vector (Qiagen, Inc.), among others, many of which are commercially available. As described in Gentz et al, Proc. Natl. Acad. Sci. USA 86:821-824 (1989), for instance, hexa-histidine provides for convenient purification of the fusion protein. The HA tag is another peptide useful for purification which corresponds to an epitope derived of influenza hemaglutinin protein, which has been described by Wilson et al., Cell 37:767 (1984), for instance.

A fusion protein of the invention may be produced by standard recombinant DNA techniques. For example, DNA fragments coding for the different polypeptide sequences are ligated together in frame in accordance with conventional techniques, for example by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers, which give rise to complementary overhangs between two consecutive gene fragments which can subsequently be annealed and reamplified to generate a chimeric gene sequence (see, for example, Current Protocols in Molecular Biology, eds. Ausubel et al. John Wiley & Sons: 1992). Moreover, many expression vectors are commercially available that already encode a fusion moiety (e.g, a GST polypeptide). A variant-encoding nucleic acid can be cloned into such an expression vector such that the fusion moiety is linked in-frame to the said variant.

The terms "functional equivalents" and "functional variants" are used interchangeably herein. Functional equivalents according to the invention are isolated DNA fragments that encode a polypeptide that exhibits a particular function of a variant as defined herein. Functional equivalents therefore also encompass biologically active fragments and are themselves encompassed within the term "a variant" of the invention.

Preferably, a functional equivalent of the invention comprises one or more of the substitutions described herein. However, a functional equivalent may comprise one or more modifications in addition to the substitutions described above.

Functional nucleic acid equivalents may typically contain silent mutations or mutations that do not alter the biological function of encoded polypeptide. Accordingly, the invention provides nucleic acid molecules encoding a variant asparaginase protein that contains changes in amino acid residues that are not essential for a particular biological activity. Such variant proteins differ in amino acid sequence from the parent asparaginase sequence from which they are derived yet retain at least one biological activity thereof, preferably they retain at least asparaginase activity. In one embodiment the isolated nucleic acid molecule comprises a nucleotide sequence encoding a protein, wherein the protein comprises a substantially homologous amino acid sequence of at least about 60%, 65%, 70%, 75%, 80%, 85%, 90%, 95%, 96%, 97%, 98%, 99% or more homologous to the parent amino acid sequence (for example that shown in SEQ ID NO: 3).

As defined herein, the term "substantially homologous" refers to a first amino acid or nucleotide sequence which contains a sufficient or minimum number of identical or equivalent (e.g., with similar side chain) amino acids or nucleotides to a second amino acid or nucleotide sequence such that the first and the second amino acid or nucleotide sequences have a common domain. For example, amino acid or nucleotide sequences which contain a common domain having about 60%, preferably 65%, more preferably 70%, even more preferably 75%, 80%, 85%, 90%, 95%, 96%, 97%, 98% or 99% identity or more are defined herein as sufficiently identical.

The skilled person will recognise that changes can be introduced by mutation into the nucleotide sequences according to the invention thereby leading to changes in the amino acid sequence of the resulting protein without substantially altering the function of such a protein.

Accordingly, the an asparaginase variant of the invention is preferably a protein which comprises an amino acid sequence at least about 60%, 65%, 70%, 75%, 80%, 85%, 90%, 95%, 96%, 97%, 98%, 99% or more homologous to the parent amino acid sequence, for example that shown in SEQ ID NO: 3, and typically also retains at least one functional activity of the parent polypeptide.

Variants of the invention, for example functional equivalents of a protein according to the invention, can also be identified e.g. by screening combinatorial libraries of mutants, e.g. truncation mutants, of the protein of the invention for asparaginase activity. In one embodiment, a variegated library of variants is generated by combinatorial mutagenesis at the nucleic acid level. A variegated library of variants can be produced by, for example, enzymatically ligating a mixture of synthetic oligonucleotides into gene sequences such that a degenerate set of potential protein sequences is expressible as individual polypeptides, or alternatively, as a set of larger fusion proteins (e.g. for phage display). There are a variety of methods that can be used to produce libraries of potential variants of the polypeptides of the invention from a degenerate oligonucleotide sequence. Methods for synthesizing degenerate oligonucleotides are known in the art (see, e.g., Narang (1983) Tetrahedron 39:3; Itakura et al. (1984) Annu. Rev. Biochem. 53:323; Itakura et al. (1984) Science 198:1056; Ike et al. (1983) Nucleic Acid Res. 11:477).

In addition, libraries of fragments of the sequence encoding a polypeptide of the invention can be used to generate a variegated population of polypeptides for screening a subsequent selection of variants. For example, a library of coding sequence fragments can be generated by treating a double stranded PCR fragment of the coding sequence of interest with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with 51 nuclease, and ligating the resulting fragment library into an expression vector. By this method, an expression library can be derived which encodes N-terminal and internal fragments of various sizes of the protein of interest.

Several techniques are known in the art for screening gene products of combinatorial libraries made by point mutations of truncation, and for screening cDNA libraries for gene products having a selected property. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a technique which enhances the frequency of functional mutants in the libraries, can be used in combination with the screening assays to identify variants of a protein of the invention (Arkin and Yourvan (1992) Proc. Natl. Acad. Sci. USA 89:7811-7815; Delgrave et al. (1993) Protein Engineering 6(3): 327-331).

Fragments of a polynucleotide according to the invention may also comprise polynucleotides not encoding functional polypeptides. Such polynucleotides may function as probes or primers for a PCR reaction.

Nucleic acids according to the invention irrespective of whether they encode functional or non-functional polypeptides can be used as hybridization probes or polymerase chain reaction (PCR) primers. Uses of the nucleic acid molecules of the present invention that do not encode a polypeptide having asparaginase activity include, inter alia, (1) in situ hybridization (e.g. FISH) to metaphase chromosomal spreads to provide precise chromosomal location of an asparaginase-encoding gene as described in Verma et al., Human Chromosomes: a Manual of Basic Techniques, Pergamon Press, New York (1988); (2) Northern blot analysis for detecting expression of asparaginase mRNA in specific tissues and/or cells; and (3) probes and primers that can be used as a diagnostic tool to analyse the presence of a nucleic acid hybridizable to such a probe or primer in a given biological (e.g. tissue) sample.

Variants of a given parent asparaginase enzyme can be obtained by the following standard procedure:
Mutagenesis (error-prone, doped oligo, spiked oligo)
Primary Screening
Identification of an improved variant (for example in relation to specific activity)
Maintenance (for example in glycerol culture, LB-Amp plates, Mini-Prep)
Streaking out on another assay plate-secondary screening
DNA Sequencing
Transformation in, for example *Aspergillus*
Cultivation, for example in 100 ml scale, purification, DSC In one embodiment the invention relates to a method of producing an asparaginase polypeptide variant according to the invention, which method comprises:
a) selecting a parent asparaginase polypeptide;
b) substituting at least one amino acid residue corresponding to any of
41, 53, 62, 63, 64, 66, 70, 71, 73, 74, 76, 77, 88, 90, 91, 101, 102, 103, 104, 106, 107, 108, 109, 111, 119, 122, 123, 132, 140, 142, 143, 145, 161, 162, 163, 164, 168, 169, 170, 195, 211, 213, 214, 215, 216, 217, 218, 219, 220, 228, 232, 233, 234, 235, 262, 267, 268, 269, 270, 271, 272, 273, 293, 295, 297, 298, 299, 300, 301, 302, 303, 304, 310, 314, 317, 318, 319, 321, 323, 324, 325, 327, 328, 329, 330, 331, 332, 333, 334, 335 or 371
said positions being defined with reference to SEQ ID NO: 3;
c) optionally substituting one or more further amino acids as defined in b);
d) preparing the variant resulting from steps a)-c);
e) determining the specific activity at least one pH and/or the pH optimum of the variant; and
f) selecting a variant having an increased specific activity at least one pH in comparison to the parent asparaginase polypeptide and/or increased pH optimum in comparison to the parent asparaginase polypeptide, thereby to produce an asparaginase polypeptide variant.

In a preferred embodiment in the method of producing an asparaginase polypeptide variant according to the invention, the parent asparaginase polypeptide has the sequence set out in SEQ ID NO: 3.

More preferably in step b) of the method according to the invention at least one amino acid residue corresponding to any of
41, 53, 63, 64, 66, 73, 74, 76, 77, 88, 90, 91, 101, 106, 111, 119, 122, 123, 132, 140, 145, 161, 170, 195, 211, 218, 228, 232, 233, 262, 267, 293, 295, 297, 299, 300, 301, 303, 304, 310, 314, 317, 321, 324, 330, 332 or 333, 371,
is substituted, said positions being defined with reference to SEQ ID NO: 3 and wherein the parent polypeptide has at least 80% homology with SEQ ID NO: 3.

Even more preferably in step b) of the method according to the invention the substituted amino acid residue corresponds to one or more of Ile at position 41, Tyr at position 53, Gly or Val or Ser at position 63, Pro at position 64, Pro at position 66, Lys at position 73, Ala at position 74, Thr at position 76, Ile at position 77, Tyr or Pro at position 88, Val at position 90, Glu at position 91, Val at position 101, Pro at position 106, Gly at position 111, Asn at position 119, His at position 122, Ala at position 123, Ser at position 132, Asn at position 140, Ser at position 145, Leu at position 161, Thr at position 170, Asp at position 195, Ser at position 211, Val at position 218, His at position 228, Val at position 232, Val at position 233, Cys or His at position 262, Tyr at position 267, Ser or Val at position 293, Ser at position 295, Ser at position 297, Ser at position 299, Ile at position 300, Pro at position 301, Ser at position 303, Thr at position 304, Val at position 310, Asp at position 314, Ile at position 317, Thr at position 321, Gly at position 324, Ser at position 330, Ala at position 332, Glu at position 333 or Met at position 371 said positions being defined with reference to SEQ ID NO: 3.

In one embodiment of the process of the invention in step e) the specific activity is determined at a pH between 4 and 8. In another embodiment of step e), prior to determining the specific activity at least one pH and/or the pH optimum of the variant, the ratio, at a specific temperature, between the asparaginase activity at pH 7 and the asparaginase activity at pH 5 of the variant may be measured and a variant may be selected wherein said ratio is higher than that of the parent asparaginase polypeptide.

In another embodiment of the process of the invention in step f) a variant is selected having an increased specific activity at least one pH, preferably at a pH between 4 and 8, in comparison to the parent polypeptide and/or having an increased pH optimum in comparison to the parent polypeptide. Preferably the variant has an increased specific activity at least one pH, preferably at a pH between 4 and 8, in comparison to the parent polypeptide and an increased pH optimum in comparison to the parent polypeptide. In another embodiment of the process of the invention in step f) a variant is selected having an increased specific activity at least one pH, preferably at a pH between 4 and 8, in comparison to the parent polypeptide.

In another embodiment, the invention features cells, e.g., transformed host cells or recombinant host cells that contain a nucleic acid encompassed by the invention. A "transformed cell" or "recombinant cell" is a cell into which (or into an ancestor of which) has been introduced, by means of recombinant DNA techniques, a nucleic acid according to the invention. Both prokaryotic and eukaryotic cells are included, e.g., bacteria, fungi, yeast, and the like, especially preferred are cells from filamentous fungi, in particular *Aspergillus niger*.

A host cell can be chosen that modulates the expression of the inserted sequences, or modifies and processes the product encoded by the incorporated nucleic acid sequence in a specific, desired fashion. Such modifications (e.g., glycosylation) and processing (e.g., cleavage) of protein products may facilitate optimal functioning of the encoded protein.

Various host cells have characteristic and specific mechanisms for post-translational processing and modification of proteins and gene products. Appropriate cell lines or host systems familiar to those of skill in the art of molecular biology and/or microbiology can be chosen to ensure the desired and correct modification and processing of the foreign protein expressed. To this end, eukaryotic host cells that possess the cellular machinery for proper processing of the primary transcript, glycosylation, and phosphorylation of the gene product can be used. Such host cells are well known in the art.

Host cells also include, but are not limited to, mammalian cell lines such as CHO, VERO, BHK, HeLa, COS, MDCK, 293, 3T3, WI38, and choroid plexus cell lines.

If desired, a stably transfected cell line can produce a variant according to the invention. A number of vectors suitable for stable transfection of mammalian cells are available to the public, methods for constructing such cell lines are also publicly known, e.g., in Ausubel et al. (supra).

The present invention further discloses a composition comprising the asparaginase variants according to the invention. The composition may optionally comprise other ingredients such as e.g. other enzymes. The asparaginase variants according to the invention or compositions comprising said asparaginases can be used in the production of a food product. In one embodiment of the invention the asparaginase variants or compositions according to the invention can be used to reduce the amount of acrylamide formed in a thermally processed food product based on an asparagine-containing raw material. They can, for example, be used in a process for the production of a food product involving at least one heating step, comprising adding one or more asparaginase enzymes to an intermediate form of said food product in said production process whereby the enzyme is added prior to said heating step in an amount that is effective in reducing the level of asparaginase that is present in said intermediate form of said food product. Such process is disclosed in WO04/030468 which process and all its preferences are herein incorporated by reference. Also in WO04/026043 suitable processes are described wherein the asparaginase according to the invention could be used. The processes disclosed in WO04/026043 and all preferences disclosed are herein incorporated by reference.

An intermediate form of the food product is defined herein as any form that occurs during the production process prior to obtaining the final form of the food product. The intermediate form may comprise the individual raw materials used and/or mixture thereof and/or mixtures with additives and/or processing aids, or subsequently processed form thereof. For example, for the food product bread, the intermediate forms comprise for example wheat, wheat flour, the initial mixture thereof with other bread ingredients such as for example water, salt, yeast and bread improving compositions, the mixed dough, the kneaded dough, the leavened dough and the partially baked dough. For example for several potato-based products, dehydrated potato flakes or granules are intermediate products, and corn masa is an intermediate product for tortilla chips.

The food product may be made from at least one raw material that is of plant origin, for example potato, tobacco, coffee, cocoa, rice, cereal, for example wheat, rye corn, maize, barley, groats, buckwheat and oat. Wheat is here and hereafter intended to encompass all known species of the *Triticum* genus, for example aestivum, durum and/or spelta. Also food products made from more than one raw material or intermediate are included in the scope of this invention, for example food products comprising both wheat (flour and/or starch) and potato. Examples of food products in which the process according the invention can be suitable for are any flour based products—for example bread, pastry, cake, pretzels, bagels, Dutch honey cake, cookies, gingerbread, gingercake and crispbread—, and any potato-based products—for example French fries, pommes frites, potato chips, croquettes.

Raw materials as cited above are known to contain substantial amounts of asparagine which is involved in the formation of acrylamide during the heating step of the production process. Alternatively, the asparagine may originate from other sources than the raw materials e.g. from protein hydrolysates, such as yeast extracts, soy hydrolysate, casein hydrolysate and the like, which are used as an additive in the food production process. A preferred production process is the baking of bread and other baked products from wheat flour and/or flours from other cereal origin. Another preferred production process is the deep-frying of potato chips from potato slices.

Preferred heating steps are those at which at least a part of the intermediate food product, e.g. the surface of the food product, is exposed to temperatures at which the formation of acrylamide is promoted, e.g. 110° C. or higher, 120° C. or higher temperatures. The heating step in the process according to the invention may be carried out in ovens, for instance at a temperature between 180-220° C., such as for the baking of bread and other bakery products, or in oil such as the frying of potato chips, for example at 160-190° C.

In another aspect, the invention provides food products obtainable by the process of the invention as described hereinbefore or by the use of the novel asparaginase as described hereinbefore to produce food products. These food products are characterized by significantly reduced acrylamide levels in comparison with the food products obtainable by production processes that do not comprise adding one or more enzymes in an amount that is effective in reducing the level of amino acids which are involved in the formation of acrylamide during said heating step. The process according to the invention can be used to obtain a decrease of the acrylamide content of the produced food product preferably more than 50%, more preferably more than 20%, even more preferably 10% and most preferably more than 5% compared to a food product obtained with the conventional process.

An additional application for the asparaginase variants according to the invention is to be employed in the therapy of tumours. The metabolism of tumour cells requires L-asparagine, which can quickly be degraded by asparaginases. The asparaginase according to the invention can also be used as an adjunct in treatment of some human leukaemia. Administration of asparaginase in experimental animals and humans leads to regression of certain lymphomas and leukemia. Therefore in one embodiment the invention relates to asparaginases or a composition according to the invention for use as medicament, e.g. in the treatment of tumors, e.g. in the treatment of lymphomas or leukaemia in animals or humans.

Asparaginase variants according to the invention may conveniently be produced in microorganisms. In the above processes, it is advantageous to use asparaginases that are obtained by recombinant DNA techniques. Such recombinant enzymes have a number of advantages, such as production at a low cost price, high yield, free from contaminating agents such as bacteria or viruses, but also free from bacterial toxins or contaminating other enzyme activities.

The invention is hereinafter illustrated by the following non-limiting Examples.

EXAMPLES

Materials & Methods

Asparaginase Assay in Order to Measure pH Dependence in Range pH=4 to pH=9

The asparaginase activity was measured using L-asparagine as substrate. The amount of ammonia that was liberated by the action of the enzyme was measured according to the Berthelot reaction. Ready-to-use reagents phenolnitroprusside and alkaline hypoclorite were obtained from Sigma. 100 µl enzyme sample was mixed with 2000 µl 100 mM L-asparagine in a mixture of 50 mM citric acid and 50 mM sodium pyrophosphate buffer of the desired pH. After incubation at 37° C. for 30 minutes the reaction was stopped by adding 400 µl 25% trichloroacetic acid, whereafter 2500 µl water was added. During the incubation the temperature was fixed at 37° C. unless indicated otherwise.

It should be understood by a person skilled in the art that enzyme dosing was chosen in such a way that after incubation under the above conditions a signal was obtained significantly above the background but still within a range where the signals obtained are proportional to the amount of enzyme added. Preferably the reaction was zero order.

After stopping the reaction, 4 µl of the incubation mixture was added to 156 µl water. Subsequently 34 µl phenol/nitroprusside solution (Sigma P6994) and 34 µl alkaline hypochlorite solution (Sigma A1727) were added. After 676 seconds of incubation at 37° C., the extinction was measured at 600 nm. Readings were corrected for the background signal by including the appropriate blanks. A sample with (TCA) inactivated enzyme was used as a blank. The assays were run on an autoanalyzer e.g. a Konelab Arena 30 (Thermo Scientific). The activity was determined using a calibration line made up by plotting the measured absorbance at 600 nm versus the known ammonium sulphate concentrations of a standard series. Activity was expressed in units, where one unit is defined as the amount of enzyme required to liberate one micromole of ammonia from L-asparagine per minute under defined assay conditions.

Asparaginase Assay in Order to Measure pH Dependence in Range pH=4 to pH=8

The method was executed in the same way as to the method described above for measurement of pH dependence of the activity for the range pH=4 to pH=9, with the difference that 100 µl enzyme sample was mixed with 2000 µl 100 mM L-asparagine in a 50 mM phosphate/citric acid buffer of the desired pH.

Asparaginase Manual Assay in Order to Measure Activity at pH=5 and pH=7

The assay was performed e.g. in microtiterplates (MTP's) or tubes. To identify asparaginases with a shifted pH-activity profile, activity was measured at pH=5 and pH=7. 10 µl enzyme sample was mixed with 190 µl 100 mM L-asparagine in 100 mM citric acid buffer pH 5.0 or 100 mM phosphate buffer pH 7.0. After incubation at room temperature and for 1 hr the reaction was stopped by adding 100 µl 12.5% trichloroacetic acid. The enzyme dosing was chosen in such a way that after 1 hour incubation at room temperature, a signal was obtained significantly above the background. After stopping the reaction, 95 µl water was added to 8 µl of the incubation mixture. Subsequently, 70 µl phenol/nitroprusside solution (Sigma P6994) and 70 µl alkaline hypochlorite solution (Sigma A1727) were added. After 60 minutes of incubation at room temperature, the extinction was measured at 620 nm. Readings were corrected for the background signal by including the appropriate blanks e.g. inactivated sample and/or supernatant from fermentation samples of empty host strains. Empty strain indicates a host strain which has not been transformed to contain the asparaginase gene. The activity was determined using a calibration line made up by plotting the measured absorbance at 620 nm versus the known ammonium sulphate concentrations of a standard series. Activity is expressed in units, where one unit is defined as the amount of enzyme required to liberate one micromole of ammonia from L-asparagine per minute under defined assay conditions.

In all assays the activity of the asparaginase samples were expressed in unit/ml.

Example 1

Fermentation, Isolation and Purification of Asparaginases According to the Invention Asparaginases of the invention were obtained by the construction of expression plasmids containing a DNA sequence encoding the asparaginase of the invention, transforming an *Aspergillus niger* strain with the plasmid and growing the *Aspergillus niger* strains as described in WO2004/030468.

After growing *Aspergillus niger* containing the proper expression plasmids cell free supernatants were prepared by centrifugation of the fermentation broth at 5000×g for 30 minutes at 4° C. If necessary the supernatants were filtered further over a Miracloth filter (Calbiochem cat#475855) and a GF/A Whatmann Glass microfiber filter (150 mm Ø), respectively, to remove any solids. To remove any fungal material the supernatants could be adjusted to pH=5 with 4N KOH and sterile filtrated over a 2 µm (bottle-top) filter with suction. The supernatants were stored until use at 4° C. or frozen at −20° C. if necessary.

In case impurities were more than 60% w/w asparaginase were purified by anion ion-exchange chromatography starting from cell free supernatants or ccUF desalted via a PD-10 column (Amersham Biosciences). The desalted material was applied to a Mono-Q or Q-Sepharose column equilibrated in 20 mM histidine buffer pH 5.96. After extensive washing the asparaginases were eluted from the column using a gradient from 0 to 1M NaCl.

The purity of the supernatant fractions containing the asparaginase activity or of the purified asparaginase fractions (determined in mg protein/ml) was checked by analytical size-exclusion chromatography (HP-SEC: High Performance Size Exclusion Chromatography, TSKgel 3000SW-XL, column 300*7,8 mm; MW range 10-300 kDa, 100 mM phosphate buffer pH7 and pH5.96). All flows were 1 ml/min (except for sample injection on the Q-Sepharose column, which was at 5 ml/min). Detection of eluted proteins was done at 280 nm. The concentration of the eluted *Aspergillus niger* wild type asparaginase was calculated from the extinction at 280 nm (A280) using a molar extinction coefficient of 10240 $M^{-1} \cdot cm^{-1}$ ($A280^{1cm,1mg/ml}$=0.28, wherein $A280^{1cm,1mg/ml}$ is the extinction at 280 nm measured with a path length of 1 cm and at a concentration of pure protein of 1 mg/ml). Measurement of the A280 was performed in a Uvikon XL Secomam spectrophotometer (Beun de Ronde, Abcoude, The Netherlands). For asparaginases corresponding to ASN15 abd ASN 16 the same extinction coefficient as that of the *Aspergillus niger* wild type asparaginase was used.

In case of impurities absorbing at 280 nm the asparaginase concentration was corrected based on the HP-SEC chromatogram by multiplying the measured A280 of the asparaginase sample by the ratio of the area under the asparaginase peak and the total area of the peaks absorbing at 280 nm. When the asparaginase peaks was not clearly separated from other peaks the peak heights instead of peak areas were taken.

For asparaginases corresponding to ASN 01 to ASN14 the asparaginase content (determined in mg protein/ml) can be determined by PAA-SDS gel electrophoresis using NuPAGE® Novex 4-12% Bis-Tris 12 well gels (Invitrogen, NP0322BOX). 1 μl of culture supernatant was incubated with 1 μl 10× NuPAGE® Sample Reducing Agent (Invitrogen, NP0004), 2.5 μl 4× NuPAGE LDS Sample Buffer (Invitrogen, NP0007) and 5.5 μl milliQ water for 10 minutes at 70° C. The resulting reduced sample was loaded on the gel. The SeeBlue® Plus2 prestained standard (Invitrogen, LC5925) was used as size marker. In addition, 0.5 μg of BSA (Sigma A9418) was loaded as calibrator for the amount of protein. The gels were run in NuPAGE® MES SDS running buffer (Invitrogen, NP0002), containing NuPAGE® Antioxidant (Invitrogen, NP0005) for 35 minutes at 200 V. Following electrophoresis, the gels were fixed for 2×30 minutes in Fix solution (7% HAc (v/v) and 10% ethanol (v/v)), stained over night with SYPRO Ruby protein gel stain (Invitrogen S12000) and de-stained in Fix solution for 2×30 minutes. Subsequently, the gels were washed with demineralised water and scanned with the Typhoon 9200 scanner (GE Healthcare). The peak volume was calculated using Image Quant TLv2003.02 software and the protein concentrations were calculated based on the BSA protein band.

Example 2

Performance of the Variant Asparaginases According to the Invention

A random library of *A. niger* asparaginase mutants (wherein the parent polypeptide was that according to SEQ ID NO: 3) was screened for mutants with a changed pH-activity profile. In order to find mutants with improved activity at more alkaline pH, the activity of the asparaginase mutants was determined at pH=5 and pH=7. Subsequently the ratio between the activity at pH=7 and the activity at pH=5 was determined. This ratio is shown in table 1. A higher ratio indicates a shift of the pH-activity profile towards pH=7.

TABLE 1

Third column: Ratio between activity at pH = 7 and activity at pH = 5 for selected mutants. Wild type (WT) is *A. niger* asparaginase (WO2004/030468). Fourth column: The pH shift of the alkaline limb of the pH-activity profile represented by the pH at which the mutant still exhibits 50% of its maximal catalytic activity. The pH-activity profiles were determined at 37° C. using cell-free supernatants. Activity was measured in the range pH = 4 to pH = 8, using a phosphate/citric acid buffer system.

| Variant | Amino acid substitution if compared with SEQ ID NO: 3 | Ratio between activity at pH = 7 and activity at pH = 5 | Alkaline pH at which still 50% activity is observed | Amino acid sequence |
|---|---|---|---|---|
|  | WT | 0.42 | 6.7 | SEQ ID NO: 3 |
| ASN01 | D63G + G132S | 1.21 | 8.0 | SEQ ID NO: 4 |
| ASN02 | D63G + D111G + R122H | 1.25 | 8.1 | SEQ ID NO: 5 |

TABLE 1-continued

Third column: Ratio between activity at pH = 7 and activity at pH = 5 for selected mutants. Wild type (WT) is *A. niger* asparaginase (WO2004/030468). Fourth column: The pH shift of the alkaline limb of the pH-activity profile represented by the pH at which the mutant still exhibits 50% of its maximal catalytic activity. The pH-activity profiles were determined at 37° C. using cell-free supernatants. Activity was measured in the range pH = 4 to pH = 8, using a phosphate/citric acid buffer system.

| Variant | Amino acid substitution if compared with SEQ ID NO: 3 | Ratio between activity at pH = 7 and activity at pH = 5 | Alkaline pH at which still 50% activity is observed | Amino acid sequence |
|---|---|---|---|---|
| ASN03 | D63V + T300I | 0.60 | 7.3 | SEQ ID NO: 6 |
| ASN04 | S64P + I310V | 0.57 | 7.2 | SEQ ID NO: 7 |
| ASN05 | T41I + S66P + V371M | 0.90 | 7.8 | SEQ ID NO: 8 |
| ASN06 | A76T + A101V | 0.88 | 7.6 | SEQ ID NO: 9 |
| ASN07 | V77I + V123A + E314D | 0.54 | 7.1 | SEQ ID NO: 10 |
| ASN08 | S88Y | 0.63 | 7.4 | SEQ ID NO: 11 |
| ASN09 | S88P + I161L + R262C | 0.73 | 7.6 | SEQ ID NO: 12 |
| ASN10 | D140N | 0.73 | 7.4 | SEQ ID NO: 13 |
| ASN11 | D91E + A170T + R262H | 0.83 | 7.5 | SEQ ID NO: 14 |
| ASN12 | L90V + K119N + Y228H + R262C | 0.62 | 7.3 | SEQ ID NO: 15 |
| ASN13 | F53Y + K119N | 0.48 | 6.9 | SEQ ID NO: 16 |
| ASN14 | G195D + A293V | 0.75 | 7.4 | SEQ ID NO: 17 |

Mutants with a higher ratio than the wild type *A. niger* asparaginase were further tested to establish to which extent the pH activity profile was shifted to alkaline pH. For these mutants a full pH-activity profile was measured and it was shown that in particular the alkaline limb of the pH-activity profile has shifted to higher pH. The pH at which the alkaline limb of the pH-activity profile shows 50% of the maximal activity of a mutant at its pH optimum is taken as an indicator for a shift of the alkaline limb of the pH activity profile compared to wild type (table 1). A shift to a higher pH indicates a higher activity under more alkaline conditions. Such mutants are in particular beneficial in applications that require more alkaline condition.

When selecting for mutants with a lower ratio between activity at pH=7 and activity at pH=5 it is observed that the alkaline limb of the pH-activity profile shifts to a lower pH (table 2).

TABLE 2

Ratio between activity at pH = 7 and activity at pH = 5 for selected mutants. Wild type (WT) is *A. niger* asparaginase (WO2004/030468). The pH-activity profiles were determined at 37° C. using cell-free supernatants. Activity was measured in the range pH = 4 to pH = 8, using a phosphate/citric acid buffer system.

| Variant | Amino acid substitution if compared with SEQ ID NO: 3 | Ratio between activity at pH = 7 and activity at pH = 5 | Alkaline pH at which still 50% activity is observed | Amino acid sequence |
|---|---|---|---|---|
|  | WT | 0.42 | 6.7 | SEQ ID NO: 3 |
| ASN15 | T73K + S74A + A293S | 0.37 | 6.5 | SEQ ID NO: 18 |

TABLE 2-continued

Ratio between activity at pH = 7 and activity at pH = 5 for selected mutants. Wild type (WT) is *A. niger* asparaginase (WO2004/030468). The pH-activity profiles were determined at 37° C. using cell-free supernatants. Activity was measured in the range pH = 4 to pH = 8, using a phosphate/citric acid buffer system.

| Variant | Amino acid substitution if compared with SEQ ID NO: 3 | Ratio between activity at pH = 7 and activity at pH = 5 | Alkaline pH at which still 50% activity is observed | Amino acid sequence |
|---|---|---|---|---|
| ASN16 | T73K + S74A + E106P + A293S + G297S + T299S + Q319A + M321T + V324G | 0.08 | 5.9 | SEQ ID NO: 19 |

The pH-Activity Dependence and the pH Optimum

The pH dependence of the asparaginase activity for the mutants was determined in 50 mM phosphate/citrate buffer for the pH range pH=4 to pH=8 using cell-free supernatants.

The pH at which the highest activity was observed for a mutant is called the pH optimum for the said mutant. In tables 3 and 4 the maximum activity observed for a mutant is set to 100% and activities of said mutant at other pH values are shown as percentage of the maximum activity observed for said mutant. In table 3 the pH-activity profile was determined for the pH range pH=4 to pH=8 using the phosphate/citric acid buffer system. In table 4 the pH-activity profile was determined for the pH range pH=4 to pH=9 using the pyrophosphate/citric acid buffer system.

TABLE 3

The pH dependence of the asparaginase activity for the mutants compared to wild type (wt) *A. niger* asparaginase (WO2004/030468). The highest activity that was observed for each asparaginase was set to 100%. Activity was determined using cell-free supernatant at 37° C. in the phosphate/citric acid buffer system.

| Variant | Amino acid substitution if compared with SEQ ID NO: 3 | pH = 4 | pH = 5 | pH = 6 | pH = 7 | pH = 8 |
|---|---|---|---|---|---|---|
| ASN03 | D63V + T300I | 79% | 100% | 91% | 60% | 16% |
| ASN04 | S64P + I310V | 99% | 100% | 84% | 57% | 16% |
| ASN05 | T41I + S66P + V371M | 88% | 99% | 100% | 89% | 40% |
| ASN07 | V77I + V123A + E314D | 100% | 100% | 81% | 54% | 15% |
| ASN09 | S88P + I161L + R262C | 89% | 100% | 93% | 73% | 33% |
| ASN10 | D140N | 77% | 95% | 100% | 69% | 11% |
| ASN12 | L90V + K119N + Y228H + R262C | 91% | 100% | 87% | 62% | 19% |
| ASN13 | F53Y + K119N | 98% | 100% | 76% | 48% | 18% |
| WT | WT | 100% | 99% | 72% | 43% | 14% |

TABLE 4

The pH dependence of the asparaginase activity for the mutants compared to wild type (wt) *A. niger* asparaginase (WO2004/030468). The highest activity that was observed for each asparaginase was set to 100%. Activity was determined with cell-free supernatants at 37° C. using the pyrophosphate/citric acid buffer system.

| Variant | Amino acid substitution if compared with SEQ ID NO: 3 | pH = 4 | pH = 5 | pH = 6 | pH = 7 | pH = 8 | pH = 9 |
|---|---|---|---|---|---|---|---|
| ASN01 | D63G + G132S | 72% | 83% | 97% | 100% | 50% | 0% |
| ASN02 | D63G + D111G + R122H | 71% | 80% | 93% | 100% | 56% | 1% |
| ASN06 | A76T + A101V | 91% | 100% | 98% | 88% | 22% | 1% |
| ASN08 | S88Y | 96% | 100% | 86% | 66% | 23% | 1% |
| ASN11 | D91E + A170T + R262H | 74% | 83% | 100% | 94% | 11% | 0% |
| ASN14 | G195D + A293V | 77% | 100% | 86% | 75% | 7% | 0% |
| WT | WT | 100% | 100% | 72% | 43% | 9% | 0% |

Apart from a shift of the alkaline limb of the pH-activity profile there is also a shift of the pH optimum towards higher pH. Both the mutants containing the mutation D63G show a shift of the pH optimum to pH=7. The D63G mutants contain additional mutations. However these additional mutations are different in each D63G mutant, while the pH-activity profiles are almost identical. Therefore D63G seems to cause the observed shift of the pH-activity profile. The pH optimum of mutant D140N, the mutant containing A170T, and the mutant containing the mutation S66P is shifted to pH=6.

The remaining mutants exhibit a more explicit pH optimum at pH=5 compared to wild type. Tables 3 and 4 show clearly the shift of the alkaline limb of the pH-activity profile towards higher pH resulting in a broader pH-activity profile with on particular increased relative activity for the range pH=6 to pH=8, while at the same time a substantial activity is also maintained in the acidic region pH=4 to pH=6.

Specific Activity as a Function of pH

The specific activity of the asparaginase variants was determined at pH=4, pH=5, pH=6, pH=7, pH=8 at 37° C. in 50 mM phosphate/citrate buffer using cell-free supernatants.

TABLE 5

The specific activity (measured by dividing the activity of a sample (in units/ml) by mg/ml asparaginase present in the sample) of the variants relative to wild type *A. niger* asparaginase (WO2004/030468) at the indicated pH values using asparagine as a substrate. For each pH the wild type specific activity was set to 100% and the activity of the mutants calculated relative to wild type asparaginase. When activity of the mutants was below 100%, the activity was omitted from the table. Activity was determined at 37° C. The amount of asparaginase protein in the cell-free supernatants was determined by performing PAA-SDS gel electroforesis experiments and scanning of the gels as is described in material and methods. For T73K + S74A + A293S and T73K + S74A + A293S + E106P + G297S + T299S + Q319A + M321T + V324G the asparaginase protein concentration was derived from an A280 measurement applying a correction for any impurities based on HP-SEC chromatography.

| Variant | Amino acid substitution if compared with SEQ ID NO: 3 | pH 4 | pH 5 | pH 6 | pH 7 | pH 8 |
|---|---|---|---|---|---|---|
| WT | WT | 100% | 100% | 100% | 100% | 100% |
| ASN01 | D63G + G132S | 86% | 96% | 156% | 254% | 408% |
| ASN02 | D63G + D111G + R122H | 87% | 101% | 156% | 282% | 543% |
| ASN03 | S64P + I310V | 89% | 91% | 106% | 120% | 105% |
| ASN05 | T41I + S66P + V371M | 164% | 187% | 260% | 392% | 527% |
| ASN06 | A76T + A101V | 64% | 71% | 97% | 148% | 227% |
| ASN08 | S88Y | 83% | 87% | 107% | 129% | 159% |
| ASN09 | S88P + I161L + R262C | 135% | 152% | 195% | 257% | 350% |
| ASN11 | D91E + A170T + R262H | 46% | 51% | 66% | 91% | 133% |
| ASN12 | L90V + K119N + Y228H + R262C | 82% | 92% | 111% | 132% | 120% |
| ASN13 | F53Y + K119N | 185% | 189% | 199% | 214% | 235% |
| ASN14 | G195D + A293V | 79% | 93% | 110% | 159% | 158% |
| ASN15 | T73K + S74A + A293S | 166% | 173% | 154% | 151% | 142% |
| ASN16 | T73K + S74A + A293S + E106P + G297S + T299S + Q319A + M321T + V324G | 106% | 189% | 125% | 37% | 8% |

Table 5 shows that the specific activity of the mutants at pH=6, pH=7 and pH=8 has been substantially improved compared to wild type asparaginase. In particular mutants T73K+S74A+A293S, T41I+S66P+V371M, S88P+I161L+R262C and F53Y+K119N are very useful because they show a higher activity over the whole pH range pH=4 to pH=8. Mutant T73K+S74A+A293S+E106P+G297S+T299S+Q319A+M321T+V324G is more active in the acidic pH region pH=4 to pH=6.

Temperature Optimum

In order to verify the dependence of the activity on the temperature the activity was measured at different temperatures. In one assay the enzyme reaction was stopped after 10 minutes, in a second assay the reaction was stopped after 30 minutes. The enzyme dosing in the 30 minutes assay was one third of dosing in the 10 minutes assay. If the enzymes are stable under the applied conditions the observed activity should be similar. In case inactivation occurs one expects activity to decrease after longer assay time. Results are shown in table 6.

TABLE 6

Temperature dependence of the activity. Assay was carried at pH = 5 in 50 mM phosphate/citric acid buffer. The enzyme dosing in 30 minutes assay was one third of dosing in 10 minutes assay. The highest activity at 10 minutes incubation time was set to 100%.

| Variant | Amino acid substitution if compared with SEQ ID NO: 3 | 50° C. 10 min | 50° C. 30 min | 60° C. 10 min | 60° C. 30 min | 70° C. 10 min | 70° C. 30 min |
|---|---|---|---|---|---|---|---|
| WT | WT | 100% | 98% | 98% | 97% | 62% | 58% |
| ASN01 | D63G + G132S | 67% | 70% | 89% | 95% | 100% | 107% |
| ASN02 | D63G + D111G + R122H | 70% | 72% | 87% | 91% | 99% | 106% |
| ASN04 | T41I + S66P + V371M | 77% | 79% | 93% | 98% | 100% | 102% |
| ASN09 | S88P + I161L + R262C | 84% | 87% | 100% | 100% | 95% | 95% |
| ASN08 | S88Y | 85% | 93% | 100% | 104% | 85% | 88% |

Table 6 indicates that the stability of the variants is very similar to wild type *Aspergillus niger* asparaginase. Mutants show no reduction in activity after 30 minutes incubation compared to 10 minutes even at 70° C., which indicates mutants are stable at least for 30 minutes at 70° C. Surprisingly it is observed that the temperature optimum of the mutants is shifted to higher temperature. For wild type the temperature optimum is at 50° C. considering the temperatures which are tested. For mutants S16A+D63G+G132S, D63G+D111G+R122H and T41I+S66P+V371M it has shifted to 70° C. Such properties are in particular useful in applications that require asparaginases working at elevated temperatures.

The invention claimed is:

1. A variant of a parent polypeptide having asparaginase activity, wherein the variant has an amino acid sequence which, when aligned with the sequence set out in SEQ ID NO: 3, comprises substitution of an amino acid residue corresponding to any of amino acids 41, 62, 63, 76, 77, 101, 104, 106, 108, 119, 122, 123, 132, 140, 142, 143, 145, 162, 163, 169, 170, 195, 213, 217, 218, 232, 233, 234, 268, 269, 270, 272, 273, 293, 297, 298, 300, 301, 304, or 371; said positions being defined with reference to SEQ ID NO: 3, and wherein the parent polypeptide has at least 90% homology with SEQ ID NO: 3.

2. A variant according to claim 1, wherein the parent polypeptide has the sequence set out in SEQ ID NO: 3.

3. A variant according to claim 1, wherein the variant has an amino acid sequence which, when aligned with the sequence set out in SEQ ID NO: 3, comprises substitution of an amino acid residue corresponding to any of amino acids 41, 63, 76, 77, 101, 106, 119, 122, 123, 132, 140, 145, 170, 195, 218, 232, 233, 293, 297, 300, 301, 304, or 371; said positions being defined with reference to SEQ ID NO: 3.

4. A variant according to claim 1, wherein the variant has an amino acid sequence which, when aligned with the sequence set out in SEQ ID NO: 3, comprises one or more of Ile at position 41, Gly or Val or Ser at position 63, Thr at position 76, Ile at position 77, Val at position 101, Pro at position 106, Asn at position 119, His at position 122, Ala at position 123, Ser at position 132, Asn at position 140, Ser at position 145, Thr at position 170, Val at position 218, Val at position 232, Val at position 233, Ser or Val at position 293, Ser at position 297, Ile at position 300, Pro at position 301, Thr at position 304, or Met at position 371; said positions being defined with reference to SEQ ID NO: 3.

5. A variant according to claim 1, wherein the variant has an amino acid sequence which, when aligned with the sequence set out in SEQ ID NO: 3, comprises substitution of an amino acid residue corresponding to any of amino acids 63, 76, 77, 101, 140, 170 or 293; said positions being defined with reference to SEQ ID NO: 3.

6. A variant according to claim 1, wherein the variant has an amino acid sequence which, when aligned with the sequence set out in SEQ ID NO: 3, comprises one or more substitution of Gly or Val at position 63, Thr at position 76, Ile at position 77, Val at position 101, Asn at position 140, Thr at position 170, Ser or Val at position 293, said positions being defined with reference to SEQ ID NO: 3.

7. A variant according to claim 1, wherein the variant comprises any one of SEQ ID NO: 4, SEQ ID NO: 5, SEQ ID NO: 6, SEQ ID NO: 8, SEQ ID NO: 9, SEQ ID NO: 10, SEQ ID NO: 13, SEQ ID NO: 14, SEQ ID NO: 15, SEQ ID NO: 16, SEQ ID NO: 17, SEQ ID NO: 18 or SEQ ID NO: 19.

8. A variant according to claim 1 which has at least 95% homology with SEQ ID NO: 3.

9. A variant according to claim 1 which has a specific activity, which is higher than that of the parent polypeptide measured at the same pH.

10. A variant according to claim 1, wherein the variant has a pH optimum which is higher than that of the parent polypeptide.

11. A variant according to claim 1 which further comprises additional substitution of amino acid residues selected from an amino acid residue corresponding to any of amino acids 53, 64, 66, 70, 71, 73, 74, 88, 90, 91, 102, 103, 107, 109, 111, 161, 164, 168, 211, 214, 215, 216, 219, 220, 228, 235, 262, 267, 271, 295, 299, 302, 303, 310, 314, 317, 318, 319, 321, 323, 324, 325, 327, 328, 329, 330, 331, 332, 333, 334, or 335, said positions being defined with reference to SEQ ID NO: 3.

12. A variant according to claim 11 which comprises from 1 to 5 additional substitutions.

13. An isolated nucleic acid encoding the variant according to claim 1.

14. A nucleic acid construct comprising the nucleic acid sequence of claim 13 operably linked to one or more control sequences capable of directing the expression of an asparaginase in a suitable expression host.

15. A recombinant expression vector comprising the nucleic acid construct of claim 14.

16. A recombinant host cell comprising the expression vector of claim 15.

17. A method for producing an asparaginase comprising cultivating the host cell of claim 16 under conditions conducive to production of the asparaginase and recovering the asparaginase.

18. A method of producing an asparaginase polypeptide variant according to claim 1, which method comprises: a) selecting a parent asparaginase polypeptide; b) substituting at least one amino acid residue corresponding to any of 41, 62, 63, 76, 77, 101, 104, 106, 108, 119, 122, 123, 132, 140, 142, 143, 145, 162, 163, 169, 170, 195, 213, 217, 218, 232, 233, 234, 268, 269, 270, 272, 273, 293, 297, 298, 300, 301, 304, or 371; said positions being defined with reference to SEQ ID NO: 3, and wherein the parent polypeptide has at least 90% homology with SEQ ID NO: 3; c) optionally substituting one or more further amino acids as defined in b); d) preparing the variant resulting from steps a)-c); e) determining the specific activity at least one pH and/or the pH optimum of the variant; and f) selecting a variant having an increased specific activity at least one pH in comparison to the parent asparaginase polypeptide and/or an increased pH optimum in comparison to the parent asparaginase polypeptide, thereby to produce an asparaginase polypeptide variant.

19. A method according to claim 18, wherein the parent asparaginase polypeptide has the sequence set out in SEQ ID NO: 3.

20. A method according to claim 18 wherein in step b) at least one amino acid residue corresponding to any of 41, 63, 76, 77, 101, 106, 119, 122, 123, 132, 140, 145, 170, 195, 218, 232, 233, 293, 297, 300, 301, 304, or 371 is substituted; said positions being defined with reference to SEQ ID NO: 3, and wherein the parent polypeptide has at least 90% homology with SEQ ID NO: 3.

21. A method according to claim 20 wherein in step b) the substituted amino acid residue corresponds to one or more of Ile at position 41, Gly or Val or Ser at position 63, Thr at position 76, Ile at position 77, Val at position 101, Pro at position 106, Asn at position 119, His at position 122, Ala at position 123, Ser at position 132, Asn at position 140, Ser at position 145, Thr at position 170, Asp at position 195, Val at position 218, Val at position 232, Val at position 233, Ser or Val at position 293, Ser at position 297, Ile at position 300, Pro at position 301, Thr at position 304, or Met at position 371; said positions being defined with reference to SEQ ID NO: 3.

22. A composition comprising the variant according to claim 1.

23. Process for the production of a food product involving at least one heating step, comprising adding one or more asparaginase enzymes according to claim 1 to an intermediate form of said food product in said production process, whereby the enzyme is added prior to said heating step in an amount that is effective in reducing the level of asparaginase that is present in said intermediate form of said food product.

24. The variant of claim 1 comprising a substitution at amino acid residue 63.

25. The variant of claim 9, wherein the specific activity of the variant protein is higher than the specific activity of the parent polypeptide at least at one pH.

26. The variant of claim 25, wherein the specific activity of the variant protein is higher at a pH from 4 to 8, than the specific activity of the parent polypeptide at the same pH.

27. A variant of a parent polypeptide having asparaginase activity, wherein the variant has an amino acid sequence which, when aligned with the sequence set out in SEQ ID NO: 3, comprises one or more of: Tyr at position 53, Pro at position 64, Lys at position 73, Ala at position 74, Thr at position 76, Ile at position 77, Tyr or Pro at position 88, Val at position 90, Glu at position 91, Gly at position 111, Asp at position 195, Ser at position 211, His at position 228, Cys or His at position 262, Tyr at position 267, Ser at position 295, Ser at position 299, Ser at position 303, Val at position 310, Asp at position 314, Ile at position 317, Ala at position 319, Thr at position 321, Gly at position 324, Ser at position 330, Ala at position 332, or Glu at position 333; said positions being defined with reference to SEQ ID NO: 3, and wherein the parent polypeptide has at least 90% homology with SEQ ID NO: 3.

28. The variant of claim 27, wherein the variant has an amino acid sequence according to SEQ ID NO: 11.

29. The variant according to claim 24 which has at least 95% homology with SEQ ID NO: 3.

* * * * *

SEQUENCE LISTING

<160> NUMBER OF SEQ ID NOS: 19

<210> SEQ ID NO 1
<211> LENGTH: 3223
<212> TYPE: DNA
<213> ORGANISM: Aspergillus niger

<400> SEQUENCE: 1

```
tgggggaac ttgcatctga gagcatcata ctagttacta ctactactac tacttgccga      60
tgaataaaca tcctgcttgt actacgcatc gccgtcttgc tgacatggag atatattttg     120
ggctccgaga gttttgatag cagtagccaa ttaactagta gatgctagta ctactctagt     180
aatttggggg cgaatgttga atccagctca tgccaattga catctggaga tctccacgag     240
acaacgagat aagatgaaat attgctgtca tgggtgataa ctagatgctt cgagaaggat     300
tcttgaggat tgcctcatcg catgggataa tatcaccctc gggtggacct tcccggctgt     360
tggggcttat cgtggaagag tcaccccga tatcggtggg ccaagccctt tatcaatcat     420
catcctatca gtttccaccc acaagatagc ctatggaccc tgattccctt ctagccacag     480
agactagtac tagtctatca tgtcgactcc atgtggagaa accctgataa gaccatgtgg     540
aggaggagat agcaagcctc cacagaaaca atatcatctc cacctgcaat cacggttgga     600
ttccgaatac acccgccgcc tggcaagcac atggggtata aaatgctgaa accaggcaag     660
atgaattgga agagaagcca gcagagacca tcgcatccgt cttcatcatg cctctcaagc     720
cgattctcct gtctgccctg gccagtctcg cctcggcctc tccgctgctc tactcgcgga     780
ccaccaatga aaccttcgtc ttcaccaatg ccaatggcct caacttcacc cagatgaaca     840
ccaccctgcc gaacgtgacc attttcgcaa cgggtaggtg gaccgagtat acctcaggta     900
gtgcgaccga tagttaaccg caactcacag gtggtaccat cgcgggctcc gattccagct     960
caaccgccac gaccggctac acctccggag cagtcggggt cctgtccctc atcgatgcgg    1020
tgccatccat gctggatgtg gccaatgttg ccggcgtcca ggtggccaac gtgggaagcg    1080
aggatatcac ctctgacatc ctgatttcca tgtccaagaa gctgaaccgc gttgtatgtg    1140
aggacccgac catggccggt gctgtcatca cccacggcac cgacaccctc gaggagactg    1200
ccttcttcct ggacgccact gtcaactgtg gcaagccaat tgtcatcgtg ggtgccatgc    1260
gcccatccac ggccatctca gctgacgggc ccttcaatct gctcgaagcc gtgacggtgg    1320
ctgcctccac gtcggcgcgc gatcgcggtg ccatggtggt catgaacgat cgcattgcct    1380
cggcctacta tgtgaccaag accaatgcca acactatgga caccttcaag gccatggaga    1440
tgggctacct tggcgagatg atctccaaca cccctttctt cttctacccg cccgtcaagc    1500
caaccggtaa ggtggccttt gacatcacca acgtgactga gatcccccgt gtggacattc    1560
tgttttctta tgaggacatg cacaacgaca ccctctacaa cgccatctcc agtggtgccc    1620
agggaattgt ggtgagtgtg atttccttga tctctctcta taaaacttgg aatggacgct    1680
gatgagaata gattgccggg gctggtgctg gaggcgtcac aacctccttc aatgaggcta    1740
tcgaggatgt catcaaccgt ttggagatcc ctgtcgtgca gagtatgcgc acagtcaatg    1800
```

-continued

```
gggaagtgcc actgtcagac gtgagcagcg acaccgccac ccacatcgcc agtggatacc   1860
taaacccgca gaagtcccgc attctgttgg gattgctgct atcccaggga agaatatca   1920
ccgaaatcgc tgacgtgttt gctctgggca cggatgcgta ggtgtcgata gaaccattgt   1980
atataataat gaccggatat tatgatcatg atagattgca atagaaagtg actggataca   2040
catcagcaaa ggataccgag ttttgccctc aggcgttcgt agaaaaagtg tatcctactg   2100
aagatcatga atcatgtctt atcttctggc ccctcgtat ccagggtgtt ggacatgcag   2160
ggtgctttgc gtctgaagga tccgagatca aattgacacg agccagagtc tgatacatcc   2220
ataatagtgg gtatatttga agtccattga tagtccttgt ttgtgtcggg caattgggtt   2280
agctagggcc tggcttggtg gcatatcgtt ggactaatag atggtagttc aattaccgac   2340
gggactgtct cccgccatta ttctcacaat tcttatcagc acattttccc tgtcgcgctt   2400
ggatctgcaa tatttatttc cctcgtcatc acattcccac gaaaagacca tccagacatc   2460
ttgctcggta ttctggaccg taagactgtt ttgaaaggca aatgtaaagc gtgattggtc   2520
gacgtcaagc ctgaccaatc tagtaagctg gtcttacttt gggtgtagac ggaggtatta   2580
ggtagtatta aggcagctag ttcgcctgca ttaccaccca ggcgaggcac gccactgctg   2640
atcaggcgcg aaatggaacg aagtgcgagg tccacttaac atgatgcgcg cggatactaa   2700
ggcgaccaag accctggatt gatcgctatg attcgcggaa ccccgcgggt tcttcacggc   2760
tttcgataac gcaggattgg atcctcccag cctcgtctct gcaagtggga ccctgaaggg   2820
ctctcctgca cgtcattact cagacactcc catcttttgc ttatttgcaa tgaatcttat   2880
gggctgaccc tcagctcggc gtgggatgcc tgaatcgttg gtgaaagtct atttgagcaa   2940
tcctagcctg ctggtagagg cggatgatta taataatcaa agcaccctat cgtaaggatg   3000
aaggcttgtc cctggtcaac catcactctg gttattgact agttgtgttt gggagacagc   3060
tgaagcccat tgtcggtaat cgtccccaaa gaatctgccc ctgcatcatg gagtcaggaa   3120
agaccgggtt tcgcacggtc gcagaaccgc atccaacacg tctagtagaa ggaggggtag   3180
ggatactcat ccgtctattg tgtatatctg caacgactaa tgt                    3223
```

<210> SEQ ID NO 2
<211> LENGTH: 1137
<212> TYPE: DNA
<213> ORGANISM: Aspergillus niger
<220> FEATURE:
<221> NAME/KEY: CDS
<222> LOCATION: (1)..(1137)

<400> SEQUENCE: 2

```
atg cct ctc aag ccg att ctc ctg tct gcc ctg gcc agt ctc gcc tcg     48
Met Pro Leu Lys Pro Ile Leu Leu Ser Ala Leu Ala Ser Leu Ala Ser
1               5                  10                  15 gcc tct ccg ctg ctc tac tcg cgg acc acc aat gaa acc ttc gtc ttc     96
Ala Ser Pro Leu Leu Tyr Ser Arg Thr Thr Asn Glu Thr Phe Val Phe
            20                  25                  30 acc aat gcc aat ggc ctc aac ttc acc cag atg aac acc acc ctg ccg    144
Thr Asn Ala Asn Gly Leu Asn Phe Thr Gln Met Asn Thr Thr Leu Pro
        35                  40                  45 aac gtg acc att ttc gca acg ggt ggt acc atc gcg ggc tcc gat tcc    192
Asn Val Thr Ile Phe Ala Thr Gly Gly Thr Ile Ala Gly Ser Asp Ser
    50                  55                  60 agc tca acc gcc acg acc ggc tac acc tcc gga gca gtc ggg gtc ctg    240
Ser Ser Thr Ala Thr Thr Gly Tyr Thr Ser Gly Ala Val Gly Val Leu
65                  70                  75                  80
```

```
tcc ctc atc gat gcg gtg cca tcc atg ctg gat gtg gcc aat gtt gcc    288
Ser Leu Ile Asp Ala Val Pro Ser Met Leu Asp Val Ala Asn Val Ala
             85                  90                  95 ggc gtc cag gtg gcc aac gtg gga agc gag gat atc acc tct gac atc    336
Gly Val Gln Val Ala Asn Val Gly Ser Glu Asp Ile Thr Ser Asp Ile
            100                 105                 110 ctg att tcc atg tcc aag aag ctg aac cgc gtt gta tgt gag gac ccg    384
Leu Ile Ser Met Ser Lys Lys Leu Asn Arg Val Val Cys Glu Asp Pro
            115                 120                 125 acc atg gcc ggt gct gtc atc acc cac ggc acc gac acc ctc gag gag    432
Thr Met Ala Gly Ala Val Ile Thr His Gly Thr Asp Thr Leu Glu Glu
130                 135                 140 act gcc ttc ttc ctg gac gcc act gtc aac tgt ggc aag cca att gtc    480
Thr Ala Phe Phe Leu Asp Ala Thr Val Asn Cys Gly Lys Pro Ile Val
145                 150                 155                 160 atc gtg ggt gcc atg cgc cca tcc acg gcc atc tca gct gac ggg ccc    528
Ile Val Gly Ala Met Arg Pro Ser Thr Ala Ile Ser Ala Asp Gly Pro
                165                 170                 175 ttc aat ctg ctc gaa gcc gtg acg gtg gct gcc tcc acg tcg gcg cgc    576
Phe Asn Leu Leu Glu Ala Val Thr Val Ala Ala Ser Thr Ser Ala Arg
            180                 185                 190 gat cgc ggt gcc atg gtg gtc atg aac gat cgc att gcc tcg gcc tac    624
Asp Arg Gly Ala Met Val Val Met Asn Asp Arg Ile Ala Ser Ala Tyr
            195                 200                 205 tat gtg acc aag acc aat gcc aac act atg gac acc ttc aag gcc atg    672
Tyr Val Thr Lys Thr Asn Ala Asn Thr Met Asp Thr Phe Lys Ala Met
            210                 215                 220 gag atg ggc tac ctt ggc gag atg atc tcc aac acc cct ttc ttc ttc    720
Glu Met Gly Tyr Leu Gly Glu Met Ile Ser Asn Thr Pro Phe Phe Phe
225                 230                 235                 240 tac ccg ccc gtc aag cca acc ggt aag gtg gcc ttt gac atc acc aac    768
Tyr Pro Pro Val Lys Pro Thr Gly Lys Val Ala Phe Asp Ile Thr Asn
                245                 250                 255 gtg act gag atc ccc cgt gtg gac att ctg ttt tct tat gag gac atg    816
Val Thr Glu Ile Pro Arg Val Asp Ile Leu Phe Ser Tyr Glu Asp Met
            260                 265                 270 cac aac gac acc ctc tac aac gcc atc tcc agt ggt gcc cag gga att    864
His Asn Asp Thr Leu Tyr Asn Ala Ile Ser Ser Gly Ala Gln Gly Ile
            275                 280                 285 gtg att gcc ggg gct ggt gct gga ggc gtc aca acc tcc ttc aat gag    912
Val Ile Ala Gly Ala Gly Ala Gly Gly Val Thr Thr Ser Phe Asn Glu
            290                 295                 300 gct atc gag gat gtc atc aac cgt ttg gag atc cct gtc gtg cag agt    960
Ala Ile Glu Asp Val Ile Asn Arg Leu Glu Ile Pro Val Val Gln Ser
305                 310                 315                 320 atg cgc aca gtc aat ggg gaa gtg cca ctg tca gac gtg agc agc gac    1008
Met Arg Thr Val Asn Gly Glu Val Pro Leu Ser Asp Val Ser Ser Asp
                325                 330                 335 acc gcc acc cac atc gcc agt gga tac cta aac ccg cag aag tcc cgc    1056
Thr Ala Thr His Ile Ala Ser Gly Tyr Leu Asn Pro Gln Lys Ser Arg
            340                 345                 350 att ctg ttg gga ttg ctg cta tcc cag gga aag aat atc acc gaa atc    1104
Ile Leu Leu Gly Leu Leu Leu Ser Gln Gly Lys Asn Ile Thr Glu Ile
            355                 360                 365 gct gac gtg ttt gct ctg ggc acg gat gcg tag                        1137
Ala Asp Val Phe Ala Leu Gly Thr Asp Ala
370                 375

<210> SEQ ID NO 3
<211> LENGTH: 378
<212> TYPE: PRT
```

<213> ORGANISM: Aspergillus niger

<400> SEQUENCE: 3

| | | | | | | | | | | | | | | | |
|---|---|---|---|---|---|---|---|---|---|---|---|---|---|---|---|
| Met | Pro | Leu | Lys | Pro | Ile | Leu | Leu | Ser | Ala | Leu | Ala | Ser | Leu | Ala | Ser |
| 1 | | | | 5 | | | | | 10 | | | | | 15 | |
| Ala | Ser | Pro | Leu | Leu | Tyr | Ser | Arg | Thr | Thr | Asn | Glu | Thr | Phe | Val | Phe |
| | | | 20 | | | | | 25 | | | | | 30 | | |
| Thr | Asn | Ala | Asn | Gly | Leu | Asn | Phe | Thr | Gln | Met | Asn | Thr | Thr | Leu | Pro |
| | | 35 | | | | | 40 | | | | | 45 | | | |
| Asn | Val | Thr | Ile | Phe | Ala | Thr | Gly | Gly | Thr | Ile | Ala | Gly | Ser | Asp | Ser |
| | 50 | | | | | 55 | | | | | 60 | | | | |
| Ser | Ser | Thr | Ala | Thr | Thr | Gly | Tyr | Thr | Ser | Gly | Ala | Val | Gly | Val | Leu |
| 65 | | | | | 70 | | | | | 75 | | | | | 80 |
| Ser | Leu | Ile | Asp | Ala | Val | Pro | Ser | Met | Leu | Asp | Val | Ala | Asn | Val | Ala |
| | | | | 85 | | | | | 90 | | | | | 95 | |
| Gly | Val | Gln | Val | Ala | Asn | Val | Gly | Ser | Glu | Asp | Ile | Thr | Ser | Asp | Ile |
| | | | 100 | | | | | 105 | | | | | 110 | | |
| Leu | Ile | Ser | Met | Ser | Lys | Lys | Leu | Asn | Arg | Val | Val | Cys | Glu | Asp | Pro |
| | | 115 | | | | | 120 | | | | | 125 | | | |
| Thr | Met | Ala | Gly | Ala | Val | Ile | Thr | His | Gly | Thr | Asp | Thr | Leu | Glu | Glu |
| 130 | | | | | 135 | | | | | 140 | | | | | |
| Thr | Ala | Phe | Phe | Leu | Asp | Ala | Thr | Val | Asn | Cys | Gly | Lys | Pro | Ile | Val |
| 145 | | | | | 150 | | | | | 155 | | | | | 160 |
| Ile | Val | Gly | Ala | Met | Arg | Pro | Ser | Thr | Ala | Ile | Ser | Ala | Asp | Gly | Pro |
| | | | | 165 | | | | | 170 | | | | | 175 | |
| Phe | Asn | Leu | Leu | Glu | Ala | Val | Thr | Val | Ala | Ala | Ser | Thr | Ser | Ala | Arg |
| | | | 180 | | | | | 185 | | | | | 190 | | |
| Asp | Arg | Gly | Ala | Met | Val | Val | Met | Asn | Asp | Arg | Ile | Ala | Ser | Ala | Tyr |
| | | 195 | | | | | 200 | | | | | 205 | | | |
| Tyr | Val | Thr | Lys | Thr | Asn | Ala | Asn | Thr | Met | Asp | Thr | Phe | Lys | Ala | Met |
| 210 | | | | | 215 | | | | | 220 | | | | | |
| Glu | Met | Gly | Tyr | Leu | Gly | Glu | Met | Ile | Ser | Asn | Thr | Pro | Phe | Phe | Phe |
| 225 | | | | | 230 | | | | | 235 | | | | | 240 |
| Tyr | Pro | Pro | Val | Lys | Pro | Thr | Gly | Lys | Val | Ala | Phe | Asp | Ile | Thr | Asn |
| | | | | 245 | | | | | 250 | | | | | 255 | |
| Val | Thr | Glu | Ile | Pro | Arg | Val | Asp | Ile | Leu | Phe | Ser | Tyr | Glu | Asp | Met |
| | | | 260 | | | | | 265 | | | | | 270 | | |
| His | Asn | Asp | Thr | Leu | Tyr | Asn | Ala | Ile | Ser | Ser | Gly | Ala | Gln | Gly | Ile |
| | | 275 | | | | | 280 | | | | | 285 | | | |
| Val | Ile | Ala | Gly | Ala | Gly | Ala | Gly | Gly | Val | Thr | Thr | Ser | Phe | Asn | Glu |
| | 290 | | | | | 295 | | | | | 300 | | | | |
| Ala | Ile | Glu | Asp | Val | Ile | Asn | Arg | Leu | Glu | Ile | Pro | Val | Val | Gln | Ser |
| 305 | | | | | 310 | | | | | 315 | | | | | 320 |
| Met | Arg | Thr | Val | Asn | Gly | Glu | Val | Pro | Leu | Ser | Asp | Val | Ser | Ser | Asp |
| | | | | 325 | | | | | 330 | | | | | 335 | |
| Thr | Ala | Thr | His | Ile | Ala | Ser | Gly | Tyr | Leu | Asn | Pro | Gln | Lys | Ser | Arg |
| | | | 340 | | | | | 345 | | | | | 350 | | |
| Ile | Leu | Leu | Gly | Leu | Leu | Leu | Ser | Gln | Gly | Lys | Asn | Ile | Thr | Glu | Ile |
| | | 355 | | | | | 360 | | | | | 365 | | | |
| Ala | Asp | Val | Phe | Ala | Leu | Gly | Thr | Asp | Ala | | | | | | |
| | 370 | | | | | 375 | | | | | | | | | |

<210> SEQ ID NO 4
<211> LENGTH: 378
<212> TYPE: PRT

```
<213> ORGANISM: Artificial Sequence
<220> FEATURE:
<223> OTHER INFORMATION: ASN 01 (mutated from Aspergillus niger)

<400> SEQUENCE: 4
```

| | | | | | | | | | | | | | | |
|---|---|---|---|---|---|---|---|---|---|---|---|---|---|---|
| Met | Pro | Leu | Lys | Pro | Ile | Leu | Leu | Ser | Ala | Leu | Ala | Ser | Leu | Ala | Ser |
| 1 | | | | 5 | | | | | 10 | | | | | 15 | |
| Ala | Ser | Pro | Leu | Leu | Tyr | Ser | Arg | Thr | Thr | Asn | Glu | Thr | Phe | Val | Phe |
| | | | 20 | | | | | 25 | | | | | 30 | | |
| Thr | Asn | Ala | Asn | Gly | Leu | Asn | Phe | Thr | Gln | Met | Asn | Thr | Thr | Leu | Pro |
| | | | 35 | | | | | 40 | | | | | 45 | | |
| Asn | Val | Thr | Ile | Phe | Ala | Thr | Gly | Gly | Thr | Ile | Ala | Gly | Ser | Gly | Ser |
| | 50 | | | | | 55 | | | | | 60 | | | | |
| Ser | Ser | Thr | Ala | Thr | Thr | Gly | Tyr | Thr | Ser | Gly | Ala | Val | Gly | Val | Leu |
| 65 | | | | | 70 | | | | | 75 | | | | | 80 |
| Ser | Leu | Ile | Asp | Ala | Val | Pro | Ser | Met | Leu | Asp | Val | Ala | Asn | Val | Ala |
| | | | | 85 | | | | | 90 | | | | | 95 | |
| Gly | Val | Gln | Val | Ala | Asn | Val | Gly | Ser | Glu | Asp | Ile | Thr | Ser | Asp | Ile |
| | | | 100 | | | | | 105 | | | | | 110 | | |
| Leu | Ile | Ser | Met | Ser | Lys | Lys | Leu | Asn | Arg | Val | Val | Cys | Glu | Asp | Pro |
| | | | 115 | | | | | 120 | | | | | 125 | | |
| Thr | Met | Ala | Ser | Ala | Val | Ile | Thr | His | Gly | Thr | Asp | Thr | Leu | Glu | Glu |
| | 130 | | | | | 135 | | | | | 140 | | | | |
| Thr | Ala | Phe | Phe | Leu | Asp | Ala | Thr | Val | Asn | Cys | Gly | Lys | Pro | Ile | Val |
| 145 | | | | | 150 | | | | | 155 | | | | | 160 |
| Ile | Val | Gly | Ala | Met | Arg | Pro | Ser | Thr | Ala | Ile | Ser | Ala | Asp | Gly | Pro |
| | | | | 165 | | | | | 170 | | | | | 175 | |
| Phe | Asn | Leu | Leu | Glu | Ala | Val | Thr | Val | Ala | Ala | Ser | Thr | Ser | Ala | Arg |
| | | | 180 | | | | | 185 | | | | | 190 | | |
| Asp | Arg | Gly | Ala | Met | Val | Val | Met | Asn | Asp | Arg | Ile | Ala | Ser | Ala | Tyr |
| | | | 195 | | | | | 200 | | | | | 205 | | |
| Tyr | Val | Thr | Lys | Thr | Asn | Ala | Asn | Thr | Met | Asp | Thr | Phe | Lys | Ala | Met |
| | 210 | | | | | 215 | | | | | 220 | | | | |
| Glu | Met | Gly | Tyr | Leu | Gly | Glu | Met | Ile | Ser | Asn | Thr | Pro | Phe | Phe |
| 225 | | | | | 230 | | | | | 235 | | | | | 240 |
| Tyr | Pro | Pro | Val | Lys | Pro | Thr | Gly | Lys | Val | Ala | Phe | Asp | Ile | Thr | Asn |
| | | | | 245 | | | | | 250 | | | | | 255 | |
| Val | Thr | Glu | Ile | Pro | Arg | Val | Asp | Ile | Leu | Phe | Ser | Tyr | Glu | Asp | Met |
| | | | 260 | | | | | 265 | | | | | 270 | | |
| His | Asn | Asp | Thr | Leu | Tyr | Asn | Ala | Ile | Ser | Ser | Gly | Ala | Gln | Gly | Ile |
| | | | 275 | | | | | 280 | | | | | 285 | | |
| Val | Ile | Ala | Gly | Ala | Gly | Ala | Gly | Gly | Val | Thr | Thr | Ser | Phe | Asn | Glu |
| | 290 | | | | | 295 | | | | | 300 | | | | |
| Ala | Ile | Glu | Asp | Val | Ile | Asn | Arg | Leu | Glu | Ile | Pro | Val | Val | Gln | Ser |
| 305 | | | | | 310 | | | | | 315 | | | | | 320 |
| Met | Arg | Thr | Val | Asn | Gly | Glu | Val | Pro | Leu | Ser | Asp | Val | Ser | Ser | Asp |
| | | | | 325 | | | | | 330 | | | | | 335 | |
| Thr | Ala | Thr | His | Ile | Ala | Ser | Gly | Tyr | Leu | Asn | Pro | Gln | Lys | Ser | Arg |
| | | | 340 | | | | | 345 | | | | | 350 | | |
| Ile | Leu | Leu | Gly | Leu | Leu | Leu | Ser | Gln | Gly | Lys | Asn | Ile | Thr | Glu | Ile |
| | | | 355 | | | | | 360 | | | | | 365 | | |
| Ala | Asp | Val | Phe | Ala | Leu | Gly | Thr | Asp | Ala |
| | 370 | | | | | 375 | | | |

```
<210> SEQ ID NO 5
```

<211> LENGTH: 378
<212> TYPE: PRT
<213> ORGANISM: Artificial Sequence
<220> FEATURE:
<223> OTHER INFORMATION: ASN 02 (mutated from Aspergillus niger)

<400> SEQUENCE: 5

```
Met Pro Leu Lys Pro Ile Leu Leu Ser Ala Leu Ala Ser Leu Ala Ser
1               5                   10                  15

Ala Ser Pro Leu Leu Tyr Ser Arg Thr Thr Asn Glu Thr Phe Val Phe
            20                  25                  30

Thr Asn Ala Asn Gly Leu Asn Phe Thr Gln Met Asn Thr Thr Leu Pro
        35                  40                  45

Asn Val Thr Ile Phe Ala Thr Gly Gly Thr Ile Ala Gly Ser Gly Ser
    50                  55                  60

Ser Ser Thr Ala Thr Thr Gly Tyr Thr Ser Gly Ala Val Gly Val Leu
65                  70                  75                  80

Ser Leu Ile Asp Ala Val Pro Ser Met Leu Asp Val Ala Asn Val Ala
                85                  90                  95

Gly Val Gln Val Ala Asn Val Gly Ser Glu Asp Ile Thr Ser Gly Ile
            100                 105                 110

Leu Ile Ser Met Ser Lys Lys Leu Asn His Val Val Cys Glu Asp Pro
        115                 120                 125

Thr Met Ala Gly Ala Val Ile Thr His Gly Thr Asp Thr Leu Glu Glu
    130                 135                 140

Thr Ala Phe Phe Leu Asp Ala Thr Val Asn Cys Gly Lys Pro Ile Val
145                 150                 155                 160

Ile Val Gly Ala Met Arg Pro Ser Thr Ala Ile Ser Ala Asp Gly Pro
                165                 170                 175

Phe Asn Leu Leu Glu Ala Val Thr Val Ala Ala Ser Thr Ser Ala Arg
            180                 185                 190

Asp Arg Gly Ala Met Val Val Met Asn Asp Arg Ile Ala Ser Ala Tyr
        195                 200                 205

Tyr Val Thr Lys Thr Asn Ala Asn Thr Met Asp Thr Phe Lys Ala Met
    210                 215                 220

Glu Met Gly Tyr Leu Gly Glu Met Ile Ser Asn Thr Pro Phe Phe Phe
225                 230                 235                 240

Tyr Pro Pro Val Lys Pro Thr Gly Lys Val Ala Phe Asp Ile Thr Asn
                245                 250                 255

Val Thr Glu Ile Pro Arg Val Ser Ile Leu Phe Ser Tyr Glu Asp Met
            260                 265                 270

His Asn Asp Thr Leu Tyr Asn Ala Ile Ser Ser Gly Ala Gln Gly Ile
        275                 280                 285

Val Ile Ala Gly Ala Gly Ala Gly Gly Val Thr Thr Ser Phe Asn Glu
    290                 295                 300

Ala Ile Glu Asp Val Ile Asn Arg Leu Glu Ile Pro Val Val Gln Ser
305                 310                 315                 320

Met Arg Thr Val Asn Gly Glu Val Pro Leu Ser Asp Val Ser Ser Asp
                325                 330                 335

Thr Ala Thr His Ile Ala Ser Gly Tyr Leu Asn Pro Gln Lys Ser Arg
            340                 345                 350

Ile Leu Leu Gly Leu Leu Ser Gln Gly Lys Asn Ile Thr Glu Ile
        355                 360                 365

Ala Asp Val Phe Ala Leu Gly Thr Asp Ala
    370                 375
```

-continued

```
<210> SEQ ID NO 6
<211> LENGTH: 378
<212> TYPE: PRT
<213> ORGANISM: Artificial Sequence
<220> FEATURE:
<223> OTHER INFORMATION: ASN 03 (mutated from Aspergillus niger)

<400> SEQUENCE: 6
```

Met Pro Leu Lys Pro Ile Leu Leu Ser Ala Leu Ala Ser Leu Ala Ser
1               5                   10                  15

Ala Ser Pro Leu Leu Tyr Ser Arg Thr Thr Asn Glu Thr Phe Val Phe
            20                  25                  30

Thr Asn Ala Asn Gly Leu Asn Phe Thr Gln Met Asn Thr Thr Leu Pro
        35                  40                  45

Asn Val Thr Ile Phe Ala Thr Gly Gly Thr Ile Ala Gly Ser Val Ser
    50                  55                  60

Ser Ser Thr Ala Thr Thr Gly Tyr Thr Ser Gly Ala Val Gly Val Leu
65                  70                  75                  80

Ser Leu Ile Asp Ala Val Pro Ser Met Leu Asp Val Ala Asn Val Ala
                85                  90                  95

Gly Val Gln Val Ala Asn Val Gly Ser Glu Asp Ile Thr Ser Asp Ile
            100                 105                 110

Leu Ile Ser Met Ser Lys Lys Leu Asn Arg Val Val Cys Glu Asp Pro
        115                 120                 125

Thr Met Ala Gly Ala Val Ile Thr His Gly Thr Asp Thr Leu Glu Glu
    130                 135                 140

Thr Ala Phe Phe Leu Asp Ala Thr Val Asn Cys Gly Lys Pro Ile Val
145                 150                 155                 160

Ile Val Gly Ala Met Arg Pro Ser Thr Ala Ile Ser Ala Asp Gly Pro
                165                 170                 175

Phe Asn Leu Leu Glu Ala Val Thr Val Ala Ala Ser Thr Ser Ala Arg
            180                 185                 190

Asp Arg Gly Ala Met Val Val Met Asn Asp Arg Ile Ala Ser Ala Tyr
        195                 200                 205

Tyr Val Thr Lys Thr Asn Ala Asn Thr Met Asp Thr Phe Lys Ala Met
    210                 215                 220

Glu Met Gly Tyr Leu Gly Glu Met Ile Ser Asn Thr Pro Phe Phe Phe
225                 230                 235                 240

Tyr Pro Pro Val Lys Pro Thr Gly Lys Val Ala Phe Asp Ile Thr Asn
                245                 250                 255

Val Thr Glu Ile Pro Arg Val Asp Ile Leu Phe Ser Tyr Glu Asp Met
            260                 265                 270

His Asn Asp Thr Leu Tyr Asn Ala Ile Ser Ser Gly Ala Gln Gly Ile
        275                 280                 285

Val Ile Ala Gly Ala Gly Ala Gly Gly Val Thr Ile Ser Phe Asn Glu
    290                 295                 300

Ala Ile Glu Asp Val Ile Asn Arg Leu Glu Ile Pro Val Val Gln Ser
305                 310                 315                 320

Met Arg Thr Val Asn Gly Glu Val Pro Leu Ser Asp Val Ser Ser Asp
                325                 330                 335

Thr Ala Thr His Ile Ala Ser Gly Tyr Leu Asn Pro Gln Lys Ser Arg
            340                 345                 350

Ile Leu Leu Gly Leu Leu Leu Ser Gln Gly Lys Asn Ile Thr Glu Ile
        355                 360                 365

Ala Asp Val Phe Ala Leu Gly Thr Asp Ala

<210> SEQ ID NO 7
<211> LENGTH: 378
<212> TYPE: PRT
<213> ORGANISM: Artificial Sequence
<220> FEATURE:
<223> OTHER INFORMATION: ASN 04 (mutated from Aspergillus niger)

<400> SEQUENCE: 7

```
Met Pro Leu Lys Pro Ile Leu Leu Ser Ala Leu Ala Ser Leu Ala Ser
1               5                   10                  15

Ala Ser Pro Leu Leu Tyr Ser Arg Thr Thr Asn Glu Thr Phe Val Phe
            20                  25                  30

Thr Asn Ala Asn Gly Leu Asn Phe Thr Gln Met Asn Thr Thr Leu Pro
        35                  40                  45

Asn Val Thr Ile Phe Ala Thr Gly Gly Thr Ile Ala Gly Ser Asp Pro
    50                  55                  60

Ser Ser Thr Ala Thr Thr Gly Tyr Thr Ser Gly Ala Val Gly Val Leu
65                  70                  75                  80

Ser Leu Ile Asp Ala Val Pro Ser Met Leu Asp Val Ala Asn Val Ala
                85                  90                  95

Gly Val Gln Val Ala Asn Val Gly Ser Glu Asp Ile Thr Ser Asp Ile
            100                 105                 110

Leu Ile Ser Met Ser Lys Lys Leu Asn Arg Val Val Cys Glu Asp Pro
        115                 120                 125

Thr Met Ala Gly Ala Val Ile Thr His Gly Thr Asp Thr Leu Glu Glu
    130                 135                 140

Thr Ala Phe Phe Leu Asp Ala Thr Val Asn Cys Gly Lys Pro Ile Val
145                 150                 155                 160

Ile Val Gly Ala Met Arg Pro Ser Thr Ala Ile Ser Ala Asp Gly Pro
                165                 170                 175

Phe Asn Leu Leu Glu Ala Val Thr Val Ala Ala Ser Thr Ser Ala Arg
            180                 185                 190

Asp Arg Gly Ala Met Val Val Met Asn Asp Arg Ile Ala Ser Ala Tyr
        195                 200                 205

Tyr Val Thr Lys Thr Asn Ala Asn Thr Met Asp Thr Phe Lys Ala Met
    210                 215                 220

Glu Met Gly Tyr Leu Gly Glu Met Ile Ser Asn Thr Pro Phe Phe Phe
225                 230                 235                 240

Tyr Pro Pro Val Lys Pro Thr Gly Lys Val Ala Phe Asp Ile Thr Asn
                245                 250                 255

Val Thr Glu Ile Pro Arg Val Asp Ile Leu Phe Ser Tyr Glu Asp Met
            260                 265                 270

His Asn Asp Thr Leu Tyr Asn Ala Ile Ser Ser Gly Ala Gln Gly Ile
        275                 280                 285

Val Ile Ala Gly Ala Gly Ala Gly Val Thr Thr Ser Phe Asn Glu
    290                 295                 300

Ala Ile Glu Asp Val Val Asn Arg Leu Glu Ile Pro Val Val Gln Ser
305                 310                 315                 320

Met Arg Thr Val Asn Gly Glu Val Pro Leu Ser Asp Val Ser Ser Asp
                325                 330                 335

Thr Ala Thr His Ile Ala Ser Gly Tyr Leu Asn Pro Gln Lys Ser Arg
            340                 345                 350

Ile Leu Leu Gly Leu Leu Leu Ser Gln Gly Lys Asn Ile Thr Glu Ile
        355                 360                 365
```

```
Ala Asp Val Phe Ala Leu Gly Thr Asp Ala
    370                 375
```

<210> SEQ ID NO 8
<211> LENGTH: 378
<212> TYPE: PRT
<213> ORGANISM: Artificial Sequence
<220> FEATURE:
<223> OTHER INFORMATION: ASN 05 (mutated from Aspergillus niger)

<400> SEQUENCE: 8

```
Met Pro Leu Lys Pro Ile Leu Leu Ser Ala Leu Ala Ser Leu Ala Ser
1               5                   10                  15

Ala Ser Pro Leu Leu Tyr Ser Arg Thr Thr Asn Glu Thr Phe Val Phe
            20                  25                  30

Thr Asn Ala Asn Gly Leu Asn Phe Ile Gln Met Asn Thr Thr Leu Pro
        35                  40                  45

Asn Val Thr Ile Phe Ala Thr Gly Gly Thr Ile Ala Gly Ser Asp Ser
    50                  55                  60

Ser Pro Thr Ala Thr Thr Gly Tyr Thr Ser Gly Ala Val Gly Val Leu
65                  70                  75                  80

Ser Leu Ile Asp Ala Val Pro Ser Met Leu Asp Val Ala Asn Val Ala
                85                  90                  95

Gly Val Gln Val Ala Asn Val Gly Ser Glu Asp Ile Thr Ser Asp Ile
            100                 105                 110

Leu Ile Ser Met Ser Lys Lys Leu Asn Arg Val Val Cys Glu Asp Pro
        115                 120                 125

Thr Met Ala Gly Ala Val Ile Thr His Gly Thr Asp Thr Leu Glu Glu
    130                 135                 140

Thr Ala Phe Phe Leu Asp Ala Thr Val Asn Cys Gly Lys Pro Ile Val
145                 150                 155                 160

Ile Val Gly Ala Met Arg Pro Ser Thr Ala Ile Ser Ala Asp Gly Pro
                165                 170                 175

Phe Asn Leu Leu Glu Ala Val Thr Val Ala Ala Ser Thr Ser Ala Arg
            180                 185                 190

Asp Arg Gly Ala Met Val Val Met Asn Asp Arg Ile Ala Ser Ala Tyr
        195                 200                 205

Tyr Val Thr Lys Thr Asn Ala Asn Thr Met Asp Thr Phe Lys Ala Met
    210                 215                 220

Glu Met Gly Tyr Leu Gly Glu Met Ile Ser Asn Thr Pro Phe Phe Phe
225                 230                 235                 240

Tyr Pro Pro Val Lys Pro Thr Gly Lys Val Ala Phe Asp Ile Thr Asn
                245                 250                 255

Val Thr Glu Ile Pro Arg Val Asp Ile Leu Phe Ser Tyr Glu Asp Met
            260                 265                 270

His Asn Asp Thr Leu Tyr Asn Ala Ile Ser Ser Gly Ala Gln Gly Ile
        275                 280                 285

Val Ile Ala Gly Ala Gly Ala Gly Gly Val Thr Thr Ser Phe Asn Glu
    290                 295                 300

Ala Ile Glu Asp Val Ile Asn Arg Leu Glu Ile Pro Val Val Gln Ser
305                 310                 315                 320

Met Arg Thr Val Asn Gly Glu Val Pro Leu Ser Asp Val Ser Ser Asp
                325                 330                 335

Thr Ala Thr His Ile Ala Ser Gly Tyr Leu Asn Pro Gln Lys Ser Arg
            340                 345                 350
```

```
Ile Leu Leu Gly Leu Leu Ser Gln Gly Lys Asn Ile Thr Glu Ile
        355                 360                 365

Ala Asp Met Phe Ala Leu Gly Thr Asp Ala
        370                 375

<210> SEQ ID NO 9
<211> LENGTH: 378
<212> TYPE: PRT
<213> ORGANISM: Artificial Sequence
<220> FEATURE:
<223> OTHER INFORMATION: ASN 06 (mutated from Aspergillus niger)

<400> SEQUENCE: 9

Met Pro Leu Lys Pro Ile Leu Ser Ala Leu Ala Ser Leu Ala Ser
1               5                   10                  15

Ala Ser Pro Leu Leu Tyr Ser Arg Thr Thr Asn Glu Thr Phe Val Phe
            20                  25                  30

Thr Asn Ala Asn Gly Leu Asn Phe Thr Gln Met Asn Thr Thr Leu Pro
        35                  40                  45

Asn Val Thr Ile Phe Ala Thr Gly Gly Thr Ile Ala Gly Ser Asp Ser
    50                  55                  60

Ser Ser Thr Ala Thr Thr Gly Tyr Thr Ser Gly Thr Val Gly Val Leu
65                  70                  75                  80

Ser Leu Ile Asp Ala Val Pro Ser Met Leu Asp Val Ala Asn Val Ala
                85                  90                  95

Gly Val Gln Val Val Asn Val Gly Ser Glu Asp Ile Thr Ser Asp Ile
            100                 105                 110

Leu Ile Ser Met Ser Lys Lys Leu Asn Arg Val Val Cys Glu Asp Pro
        115                 120                 125

Thr Met Ala Gly Ala Val Ile Thr His Gly Thr Asp Thr Leu Glu Glu
    130                 135                 140

Thr Ala Phe Phe Leu Asp Ala Thr Val Asn Cys Gly Lys Pro Ile Val
145                 150                 155                 160

Ile Val Gly Ala Met Arg Pro Ser Thr Ala Ile Ser Ala Asp Gly Pro
                165                 170                 175

Phe Asn Leu Leu Glu Ala Val Thr Val Ala Ala Ser Thr Ser Ala Arg
            180                 185                 190

Asp Arg Gly Ala Met Val Val Met Asn Asp Arg Ile Ala Ser Ala Tyr
        195                 200                 205

Tyr Val Thr Lys Thr Asn Ala Asn Thr Met Asp Thr Phe Lys Ala Met
    210                 215                 220

Glu Met Gly Tyr Leu Gly Glu Met Ile Ser Asn Thr Pro Phe Phe Phe
225                 230                 235                 240

Tyr Pro Pro Val Lys Pro Thr Gly Lys Val Ala Phe Asp Ile Thr Asn
                245                 250                 255

Val Thr Glu Ile Pro Arg Val Asp Ile Leu Phe Ser Tyr Glu Asp Met
            260                 265                 270

His Asn Asp Thr Leu Tyr Asn Ala Ile Ser Ser Gly Ala Gln Gly Ile
        275                 280                 285

Val Ile Ala Gly Ala Gly Ala Gly Val Thr Thr Ser Phe Asn Glu
    290                 295                 300

Ala Ile Glu Asp Val Ile Asn Arg Leu Glu Ile Pro Val Val Gln Ser
305                 310                 315                 320

Met Arg Thr Val Asn Gly Glu Val Pro Leu Ser Asp Val Ser Ser Asp
                325                 330                 335

Thr Ala Thr His Ile Ala Ser Gly Tyr Leu Asn Pro Gln Lys Ser Arg
```

```
                340             345             350
Ile Leu Leu Gly Leu Leu Ser Gln Gly Lys Asn Ile Thr Glu Ile
            355             360             365

Ala Asp Val Phe Ala Leu Gly Thr Asp Ala
    370             375

<210> SEQ ID NO 10
<211> LENGTH: 378
<212> TYPE: PRT
<213> ORGANISM: Artificial Sequence
<220> FEATURE:
<223> OTHER INFORMATION: ASN 07 (mutated from Aspergillus niger)

<400> SEQUENCE: 10

Met Pro Leu Lys Pro Ile Leu Leu Ser Ala Leu Ala Ser Leu Ala Ser
1               5                   10                  15

Ala Ser Pro Leu Leu Tyr Ser Arg Thr Thr Asn Glu Thr Phe Val Phe
                20                  25                  30

Thr Asn Ala Asn Gly Leu Asn Phe Thr Gln Met Asn Thr Thr Leu Pro
            35                  40                  45

Asn Val Thr Ile Phe Ala Thr Gly Gly Thr Ile Ala Gly Ser Asp Ser
50                  55                  60

Ser Ser Thr Ala Thr Thr Gly Tyr Thr Ser Gly Ala Ile Gly Val Leu
65                  70                  75                  80

Ser Leu Ile Asp Ala Val Pro Ser Met Leu Asp Val Ala Asn Val Ala
                85                  90                  95

Gly Val Gln Val Ala Asn Val Gly Ser Glu Asp Ile Thr Ser Asp Ile
            100                 105                 110

Leu Ile Ser Met Ser Lys Lys Leu Asn Arg Ala Val Cys Glu Asp Pro
        115                 120                 125

Thr Met Ala Gly Ala Val Ile Thr His Gly Thr Asp Thr Leu Glu Glu
130                 135                 140

Thr Ala Phe Phe Leu Asp Ala Thr Val Asn Cys Gly Lys Pro Ile Val
145                 150                 155                 160

Ile Val Gly Ala Met Arg Pro Ser Thr Ala Ile Ser Ala Asp Gly Pro
                165                 170                 175

Phe Asn Leu Leu Glu Ala Val Thr Val Ala Ala Ser Thr Ser Ala Arg
            180                 185                 190

Asp Arg Gly Ala Met Val Val Met Asn Asp Arg Ile Ala Ser Ala Tyr
        195                 200                 205

Tyr Val Thr Lys Thr Asn Ala Asn Thr Met Asp Thr Phe Lys Ala Met
210                 215                 220

Glu Met Gly Tyr Leu Gly Glu Met Ile Ser Asn Thr Pro Phe Phe Phe
225                 230                 235                 240

Tyr Pro Pro Val Lys Pro Thr Gly Lys Val Ala Phe Asp Ile Thr Asn
                245                 250                 255

Val Thr Glu Ile Pro Arg Val Asp Ile Leu Phe Ser Tyr Glu Asp Met
            260                 265                 270

His Asn Asp Thr Leu Tyr Asn Ala Ile Ser Ser Gly Ala Gln Gly Ile
        275                 280                 285

Val Ile Ala Gly Ala Gly Ala Gly Gly Val Thr Thr Ser Phe Asn Glu
290                 295                 300

Ala Ile Glu Asp Val Ile Asn Arg Leu Asp Ile Pro Val Val Gln Ser
305                 310                 315                 320

Met Arg Thr Val Asn Gly Glu Val Pro Leu Ser Asp Val Ser Ser Asp
                325                 330                 335
```

```
Thr Ala Thr His Ile Ala Ser Gly Tyr Leu Asn Pro Gln Lys Ser Arg
            340                 345                 350

Ile Leu Leu Gly Leu Leu Ser Gln Gly Lys Asn Ile Thr Glu Ile
        355                 360                 365

Ala Asp Val Phe Ala Leu Gly Thr Asp Ala
        370                 375

<210> SEQ ID NO 11
<211> LENGTH: 378
<212> TYPE: PRT
<213> ORGANISM: Artificial Sequence
<220> FEATURE:
<223> OTHER INFORMATION: ASN 08 (mutated from Aspergillus niger)

<400> SEQUENCE: 11

Met Pro Leu Lys Pro Ile Leu Leu Ser Ala Leu Ala Ser Leu Ala Ser
1               5                   10                  15

Ala Ser Pro Leu Leu Tyr Ser Arg Thr Thr Asn Glu Thr Phe Val Phe
            20                  25                  30

Thr Asn Ala Asn Gly Leu Asn Phe Thr Gln Met Asn Thr Thr Leu Pro
        35                  40                  45

Asn Val Thr Ile Phe Ala Thr Gly Gly Thr Ile Ala Gly Ser Asp Ser
    50                  55                  60

Ser Ser Thr Ala Thr Thr Gly Tyr Thr Ser Gly Ala Val Gly Val Leu
65                  70                  75                  80

Ser Leu Ile Asp Ala Val Pro Tyr Met Leu Asp Val Ala Asn Val Ala
                85                  90                  95

Gly Val Gln Val Ala Asn Val Gly Ser Glu Asp Ile Thr Ser Asp Ile
            100                 105                 110

Leu Ile Ser Met Ser Lys Lys Leu Asn Arg Val Val Cys Glu Asp Pro
        115                 120                 125

Thr Met Ala Gly Ala Val Ile Thr His Gly Thr Asp Thr Leu Glu Glu
    130                 135                 140

Thr Ala Phe Phe Leu Asp Ala Thr Val Asn Cys Gly Lys Pro Ile Val
145                 150                 155                 160

Ile Val Gly Ala Met Arg Pro Ser Thr Ala Ile Ser Ala Asp Gly Pro
                165                 170                 175

Phe Asn Leu Leu Glu Ala Val Thr Val Ala Ala Ser Thr Ser Ala Arg
            180                 185                 190

Asp Arg Gly Ala Met Val Val Met Asn Asp Arg Ile Ala Ser Ala Tyr
        195                 200                 205

Tyr Val Thr Lys Thr Asn Ala Asn Thr Met Asp Thr Phe Lys Ala Met
    210                 215                 220

Glu Met Gly Tyr Leu Gly Glu Met Ile Ser Asn Thr Pro Phe Phe Phe
225                 230                 235                 240

Tyr Pro Pro Val Lys Pro Thr Gly Lys Val Ala Phe Asp Ile Thr Asn
                245                 250                 255

Val Thr Glu Ile Pro Arg Val Asp Ile Leu Phe Ser Tyr Glu Asp Met
            260                 265                 270

His Asn Asp Thr Leu Tyr Asn Ala Ile Ser Ser Gly Ala Gln Gly Ile
        275                 280                 285

Val Ile Ala Gly Ala Gly Ala Gly Val Thr Thr Ser Phe Asn Glu
    290                 295                 300

Ala Ile Glu Asp Val Ile Asn Arg Leu Glu Ile Pro Val Val Gln Ser
305                 310                 315                 320
```

```
Met Arg Thr Val Asn Gly Glu Val Pro Leu Ser Asp Val Ser Ser Asp
            325                 330                 335

Thr Ala Thr His Ile Ala Ser Gly Tyr Leu Asn Pro Gln Lys Ser Arg
            340                 345                 350

Ile Leu Leu Gly Leu Leu Leu Ser Gln Gly Lys Asn Ile Thr Glu Ile
        355                 360                 365

Ala Asp Val Phe Ala Leu Gly Thr Asp Ala
        370                 375

<210> SEQ ID NO 12
<211> LENGTH: 378
<212> TYPE: PRT
<213> ORGANISM: Artificial Sequence
<220> FEATURE:
<223> OTHER INFORMATION: ASN 09 (mutated from Aspergillus niger)

<400> SEQUENCE: 12

Met Pro Leu Lys Pro Ile Leu Leu Ser Ala Leu Ala Ser Leu Ala Ser
1               5                   10                  15

Ala Ser Pro Leu Leu Tyr Ser Arg Thr Thr Asn Glu Thr Phe Val Phe
            20                  25                  30

Thr Asn Ala Asn Gly Leu Asn Phe Thr Gln Met Asn Thr Thr Leu Pro
        35                  40                  45

Asn Val Thr Ile Phe Ala Thr Gly Thr Ile Ala Gly Ser Asp Ser
    50                  55                  60

Ser Ser Thr Ala Thr Thr Gly Tyr Thr Ser Gly Ala Val Gly Val Leu
65                  70                  75                  80

Ser Leu Ile Asp Ala Val Pro Pro Met Leu Asp Val Ala Asn Val Ala
                85                  90                  95

Gly Val Gln Val Ala Asn Val Gly Ser Glu Asp Ile Thr Ser Asp Ile
            100                 105                 110

Leu Ile Ser Met Ser Lys Lys Leu Asn Arg Val Val Cys Glu Asp Pro
        115                 120                 125

Thr Met Ala Gly Ala Val Ile Thr His Gly Thr Asp Thr Leu Glu Glu
    130                 135                 140

Thr Ala Phe Phe Leu Asp Ala Thr Val Asn Cys Gly Lys Pro Ile Val
145                 150                 155                 160

Leu Val Gly Ala Met Arg Pro Ser Thr Ala Ile Ser Ala Asp Gly Pro
                165                 170                 175

Phe Asn Leu Leu Glu Ala Val Thr Val Ala Ala Ser Thr Ser Ala Arg
            180                 185                 190

Asp Arg Gly Ala Met Val Val Met Asn Asp Arg Ile Ala Ser Ala Tyr
        195                 200                 205

Tyr Val Thr Lys Thr Asn Ala Asn Thr Met Asp Thr Phe Lys Ala Met
    210                 215                 220

Glu Met Gly Tyr Leu Gly Glu Met Ile Ser Asn Thr Pro Phe Phe
225                 230                 235                 240

Tyr Pro Pro Val Lys Pro Thr Gly Lys Val Ala Phe Asp Ile Thr Asn
                245                 250                 255

Val Thr Glu Ile Pro Cys Val Asp Ile Leu Phe Ser Tyr Glu Asp Met
            260                 265                 270

His Asn Asp Thr Leu Tyr Asn Ala Ile Ser Ser Gly Ala Gln Gly Ile
        275                 280                 285

Val Ile Ala Gly Ala Gly Ala Gly Gly Val Thr Thr Ser Phe Asn Glu
    290                 295                 300

Ala Ile Glu Asp Val Ile Asn Arg Leu Glu Ile Pro Val Val Gln Ser
```

```
                305                 310                 315                 320
Met Arg Thr Val Asn Gly Glu Val Pro Leu Ser Asp Val Ser Ser Asp
                    325                 330                 335

Thr Ala Thr His Ile Ala Ser Gly Tyr Leu Asn Pro Gln Lys Ser Arg
                340                 345                 350

Ile Leu Leu Gly Leu Leu Ser Gln Gly Lys Asn Ile Thr Glu Ile
        355                 360                 365

Ala Asp Val Phe Ala Leu Gly Thr Asp Ala
    370                 375

<210> SEQ ID NO 13
<211> LENGTH: 378
<212> TYPE: PRT
<213> ORGANISM: Artificial Sequence
<220> FEATURE:
<223> OTHER INFORMATION: ASN 10 (mutated from Aspergillus niger)

<400> SEQUENCE: 13

Met Pro Leu Lys Pro Ile Leu Leu Ser Ala Leu Ala Ser Leu Ala Ser
1               5                   10                  15

Ala Ser Pro Leu Leu Tyr Ser Arg Thr Thr Asn Glu Thr Phe Val Phe
            20                  25                  30

Thr Asn Ala Asn Gly Leu Asn Phe Thr Gln Met Asn Thr Thr Leu Pro
        35                  40                  45

Asn Val Thr Ile Phe Ala Thr Gly Thr Ile Ala Gly Ser Asp Ser
    50                  55                  60

Ser Ser Thr Ala Thr Thr Gly Tyr Thr Ser Gly Ala Val Gly Val Leu
65                  70                  75                  80

Ser Leu Ile Asp Ala Val Pro Ser Met Leu Asp Val Ala Asn Val Ala
                85                  90                  95

Gly Val Gln Val Ala Asn Val Gly Ser Glu Asp Ile Thr Ser Asp Ile
            100                 105                 110

Leu Ile Ser Met Ser Lys Lys Leu Asn Arg Val Val Cys Glu Asp Pro
        115                 120                 125

Thr Met Ala Gly Ala Val Ile Thr His Gly Thr Asn Thr Leu Glu Glu
    130                 135                 140

Thr Ala Phe Phe Leu Asp Ala Thr Val Asn Cys Gly Lys Pro Ile Val
145                 150                 155                 160

Ile Val Gly Ala Met Arg Pro Ser Thr Ala Ile Ser Ala Asp Gly Pro
                165                 170                 175

Phe Asn Leu Leu Glu Ala Val Thr Val Ala Ala Ser Thr Ser Ala Arg
            180                 185                 190

Asp Arg Gly Ala Met Val Val Met Asn Asp Arg Ile Ala Ser Ala Tyr
        195                 200                 205

Tyr Val Thr Lys Thr Asn Ala Asn Thr Met Asp Thr Phe Lys Ala Met
    210                 215                 220

Glu Met Gly Tyr Leu Gly Glu Met Ile Ser Asn Thr Pro Phe Phe Phe
225                 230                 235                 240

Tyr Pro Pro Val Lys Pro Thr Gly Lys Val Ala Phe Asp Ile Thr Asn
                245                 250                 255

Val Thr Glu Ile Pro Arg Val Asp Ile Leu Phe Ser Tyr Glu Asp Met
            260                 265                 270

His Asn Asp Thr Leu Tyr Asn Ala Ile Ser Ser Gly Ala Gln Gly Ile
        275                 280                 285

Val Ile Ala Gly Ala Gly Ala Gly Gly Val Thr Thr Ser Phe Asn Glu
    290                 295                 300
```

```
Ala Ile Glu Asp Val Ile Asn Arg Leu Glu Ile Pro Val Val Gln Ser
305                 310                 315                 320

Met Arg Thr Val Asn Gly Glu Val Pro Leu Ser Asp Val Ser Ser Asp
                325                 330                 335

Thr Ala Thr His Ile Ala Ser Gly Tyr Leu Asn Pro Gln Lys Ser Arg
                340                 345                 350

Ile Leu Leu Gly Leu Leu Leu Ser Gln Gly Lys Asn Ile Thr Glu Ile
            355                 360                 365

Ala Asp Val Phe Ala Leu Gly Thr Asp Ala
            370                 375

<210> SEQ ID NO 14
<211> LENGTH: 378
<212> TYPE: PRT
<213> ORGANISM: Artificial Sequence
<220> FEATURE:
<223> OTHER INFORMATION: ASN 11 (mutated from Aspergillus niger)

<400> SEQUENCE: 14

Met Pro Leu Lys Pro Ile Leu Leu Ser Ala Leu Ala Ser Leu Ala Ser
1               5                   10                  15

Ala Ser Pro Leu Leu Tyr Ser Arg Thr Thr Asn Glu Thr Phe Val Phe
                20                  25                  30

Thr Asn Ala Asn Gly Leu Asn Phe Thr Gln Met Asn Thr Thr Leu Pro
            35                  40                  45

Asn Val Thr Ile Phe Ala Thr Gly Gly Thr Ile Ala Gly Ser Asp Ser
        50                  55                  60

Ser Ser Thr Ala Thr Thr Gly Tyr Thr Ser Gly Ala Val Gly Val Leu
65                  70                  75                  80

Ser Leu Ile Asp Ala Val Pro Ser Met Leu Glu Val Ala Asn Val Ala
                85                  90                  95

Gly Val Gln Val Ala Asn Val Gly Ser Glu Asp Ile Thr Ser Asp Ile
            100                 105                 110

Leu Ile Ser Met Ser Lys Lys Leu Asn Arg Val Val Cys Glu Asp Pro
        115                 120                 125

Thr Met Ala Gly Ala Val Ile Thr His Gly Thr Asp Thr Leu Glu Glu
130                 135                 140

Thr Ala Phe Phe Leu Asp Ala Thr Val Asn Cys Gly Lys Pro Ile Val
145                 150                 155                 160

Ile Val Gly Ala Met Arg Pro Ser Thr Thr Ile Ser Ala Asp Gly Pro
                165                 170                 175

Phe Asn Leu Leu Glu Ala Val Thr Val Ala Ala Ser Thr Ser Ala Arg
            180                 185                 190

Asp Arg Gly Ala Met Val Val Met Asn Asp Arg Ile Ala Ser Ala Tyr
        195                 200                 205

Tyr Val Thr Lys Thr Asn Ala Asn Thr Met Asp Thr Phe Lys Ala Met
210                 215                 220

Glu Met Gly Tyr Leu Gly Glu Met Ile Ser Asn Thr Pro Phe Phe Phe
225                 230                 235                 240

Tyr Pro Pro Val Lys Pro Thr Gly Lys Val Ala Phe Asp Ile Thr Asn
                245                 250                 255

Val Thr Glu Ile Pro His Val Asp Ile Leu Phe Ser Tyr Glu Asp Met
            260                 265                 270

His Asn Asp Thr Leu Tyr Asn Ala Ile Ser Ser Gly Ala Gln Gly Ile
        275                 280                 285
```

```
Val Ile Ala Gly Ala Gly Ala Gly Gly Val Thr Thr Ser Phe Asn Glu
            290                 295                 300

Ala Ile Glu Asp Val Ile Asn Arg Leu Glu Ile Pro Val Val Gln Ser
305                 310                 315                 320

Met Arg Thr Val Asn Gly Glu Val Pro Leu Ser Asp Val Ser Ser Asp
                325                 330                 335

Thr Ala Thr His Ile Ala Ser Gly Tyr Leu Asn Pro Gln Lys Ser Arg
            340                 345                 350

Ile Leu Leu Gly Leu Leu Ser Gln Gly Lys Asn Ile Thr Glu Ile
            355                 360                 365

Ala Asp Val Phe Ala Leu Gly Thr Asp Ala
            370                 375

<210> SEQ ID NO 15
<211> LENGTH: 378
<212> TYPE: PRT
<213> ORGANISM: Artificial Sequence
<220> FEATURE:
<223> OTHER INFORMATION: ASN 12 (mutated from Aspergillus niger)

<400> SEQUENCE: 15

Met Pro Leu Lys Pro Ile Leu Leu Ser Ala Leu Ala Ser Leu Ala Ser
1               5                   10                  15

Ala Ser Pro Leu Leu Tyr Ser Arg Thr Thr Asn Glu Thr Phe Val Phe
            20                  25                  30

Thr Asn Ala Asn Gly Leu Asn Phe Thr Gln Met Asn Thr Thr Leu Pro
        35                  40                  45

Asn Val Thr Ile Phe Ala Thr Gly Gly Thr Ile Ala Gly Ser Asp Ser
50                  55                  60

Ser Ser Thr Ala Thr Thr Gly Tyr Thr Ser Gly Ala Val Gly Val Leu
65                  70                  75                  80

Ser Leu Ile Asp Ala Val Pro Ser Met Val Asp Val Ala Asn Val Ala
                85                  90                  95

Gly Val Gln Val Ala Asn Val Gly Ser Glu Asp Ile Thr Ser Asp Ile
            100                 105                 110

Leu Ile Ser Met Ser Lys Asn Leu Asn Arg Val Val Cys Glu Asp Pro
            115                 120                 125

Thr Met Ala Gly Ala Val Ile Thr His Gly Thr Asp Thr Leu Glu Glu
        130                 135                 140

Thr Ala Phe Phe Leu Asp Ala Thr Val Asn Cys Gly Lys Pro Ile Val
145                 150                 155                 160

Ile Val Gly Ala Met Arg Pro Ser Thr Ala Ile Ser Ala Asp Gly Pro
                165                 170                 175

Phe Asn Leu Leu Glu Ala Val Thr Val Ala Ala Ser Thr Ser Ala Arg
            180                 185                 190

Asp Arg Gly Ala Met Val Val Met Asn Asp Arg Ile Ala Ser Ala Tyr
        195                 200                 205

Tyr Val Thr Lys Thr Asn Ala Asn Thr Met Asp Thr Phe Lys Ala Met
210                 215                 220

Glu Met Gly His Leu Gly Glu Met Ile Ser Asn Thr Pro Phe Phe Phe
225                 230                 235                 240

Tyr Pro Pro Val Lys Pro Thr Gly Lys Val Ala Phe Asp Ile Thr Asn
                245                 250                 255

Val Thr Glu Ile Pro Cys Val Asp Ile Leu Phe Ser Tyr Glu Asp Met
            260                 265                 270

His Asn Asp Thr Leu Tyr Asn Ala Ile Ser Ser Gly Ala Gln Gly Ile
```

```
                 275                 280                 285
Val Ile Ala Gly Ala Gly Ala Gly Gly Val Thr Thr Ser Phe Asn Glu
    290                 295                 300

Ala Ile Glu Asp Val Ile Asn Arg Leu Glu Ile Pro Val Val Gln Ser
305                 310                 315                 320

Met Arg Thr Val Asn Gly Glu Val Pro Leu Ser Asp Val Ser Ser Asp
                325                 330                 335

Thr Ala Thr His Ile Ala Ser Gly Tyr Leu Asn Pro Gln Lys Ser Arg
                340                 345                 350

Ile Leu Leu Gly Leu Leu Leu Ser Gln Gly Lys Asn Ile Thr Glu Ile
                355                 360                 365

Ala Asp Val Phe Ala Leu Gly Thr Asp Ala
    370                 375

<210> SEQ ID NO 16
<211> LENGTH: 378
<212> TYPE: PRT
<213> ORGANISM: Artificial Sequence
<220> FEATURE:
<223> OTHER INFORMATION: ASN 13 (mutated from Aspergillus niger)

<400> SEQUENCE: 16

Met Pro Leu Lys Pro Ile Leu Leu Ser Ala Leu Ala Ser Leu Ala Ser
1               5                   10                  15

Ala Ser Pro Leu Leu Tyr Ser Arg Thr Thr Asn Glu Thr Phe Val Phe
                20                  25                  30

Thr Asn Ala Asn Gly Leu Asn Phe Thr Gln Met Asn Thr Thr Leu Pro
            35                  40                  45

Asn Val Thr Ile Tyr Ala Thr Gly Gly Thr Ile Ala Gly Ser Asp Ser
    50                  55                  60

Ser Ser Thr Ala Thr Thr Gly Tyr Thr Ser Gly Ala Val Gly Val Leu
65                  70                  75                  80

Ser Leu Ile Asp Ala Val Pro Ser Met Leu Asp Val Ala Asn Val Ala
                85                  90                  95

Gly Val Gln Val Ala Asn Val Gly Ser Glu Asp Ile Thr Ser Asp Ile
            100                 105                 110

Leu Ile Ser Met Ser Lys Asn Leu Asn Arg Val Val Cys Glu Asp Pro
        115                 120                 125

Thr Met Ala Gly Ala Val Ile Thr His Gly Thr Asp Thr Leu Glu Glu
130                 135                 140

Thr Ala Phe Phe Leu Asp Ala Thr Val Asn Cys Gly Lys Pro Ile Val
145                 150                 155                 160

Ile Val Gly Ala Met Arg Pro Ser Thr Ala Ile Ser Ala Asp Gly Pro
                165                 170                 175

Phe Asn Leu Leu Glu Ala Val Thr Val Ala Ala Ser Thr Ser Ala Arg
            180                 185                 190

Asp Arg Gly Ala Met Val Val Met Asn Asp Arg Ile Ala Ser Ala Tyr
        195                 200                 205

Tyr Val Thr Lys Thr Asn Ala Asn Thr Met Asp Thr Phe Lys Ala Met
    210                 215                 220

Glu Met Gly Tyr Leu Gly Glu Met Ile Ser Asn Thr Pro Phe Phe Phe
225                 230                 235                 240

Tyr Pro Pro Val Lys Pro Thr Gly Lys Val Ala Phe Asp Ile Thr Asn
                245                 250                 255

Val Thr Glu Ile Pro Arg Val Asp Ile Leu Phe Ser Tyr Glu Asp Met
            260                 265                 270
```

His Asn Asp Thr Leu Tyr Asn Ala Ile Ser Ser Gly Ala Gln Gly Ile
            275                 280                 285

Val Ile Ala Gly Ala Gly Gly Val Thr Thr Ser Phe Asn Glu
            290                 295                 300

Ala Ile Glu Asp Val Ile Asn Arg Leu Glu Ile Pro Val Val Gln Ser
305                 310                 315                 320

Met Arg Thr Val Asn Gly Glu Val Pro Leu Ser Asp Val Ser Ser Asp
                325                 330                 335

Thr Ala Thr His Ile Ala Ser Gly Tyr Leu Asn Pro Gln Lys Ser Arg
            340                 345                 350

Ile Leu Leu Gly Leu Leu Leu Ser Gln Gly Lys Asn Ile Thr Glu Ile
            355                 360                 365

Ala Asp Val Phe Ala Leu Gly Thr Asp Ala
            370                 375

<210> SEQ ID NO 17
<211> LENGTH: 378
<212> TYPE: PRT
<213> ORGANISM: Artificial Sequence
<220> FEATURE:
<223> OTHER INFORMATION: ASN 14 (mutated from Aspergillus niger)

<400> SEQUENCE: 17

Met Pro Leu Lys Pro Ile Leu Leu Ser Ala Leu Ala Ser Leu Ala Ser
1               5                   10                  15

Ala Ser Pro Leu Leu Tyr Ser Arg Thr Thr Asn Glu Thr Phe Val Phe
            20                  25                  30

Thr Asn Ala Asn Gly Leu Asn Phe Thr Gln Met Asn Thr Thr Leu Pro
        35                  40                  45

Asn Val Thr Ile Phe Ala Thr Gly Gly Thr Ile Ala Gly Ser Asp Ser
    50                  55                  60

Ser Ser Thr Ala Thr Thr Gly Tyr Thr Ser Gly Ala Val Gly Val Leu
65                  70                  75                  80

Ser Leu Ile Asp Ala Val Pro Ser Met Leu Asp Val Ala Asn Val Ala
                85                  90                  95

Gly Val Gln Val Ala Asn Val Gly Ser Glu Asp Ile Thr Ser Asp Ile
            100                 105                 110

Leu Ile Ser Met Ser Lys Lys Leu Asn Arg Val Val Cys Glu Asp Pro
            115                 120                 125

Thr Met Ala Gly Ala Val Ile Thr His Gly Thr Asp Thr Leu Glu Glu
        130                 135                 140

Thr Ala Phe Phe Leu Asp Ala Thr Val Asn Cys Gly Lys Pro Ile Val
145                 150                 155                 160

Ile Val Gly Ala Met Arg Pro Ser Thr Ala Ile Ser Ala Asp Gly Pro
                165                 170                 175

Phe Asn Leu Leu Glu Ala Val Thr Val Ala Ala Ser Ser Ser Ala Arg
            180                 185                 190

Asp Arg Asp Ala Met Val Val Met Asn Asp Arg Ile Ala Ser Ala Tyr
            195                 200                 205

Tyr Val Thr Lys Thr Asn Ala Asn Thr Met Asp Thr Phe Lys Ala Met
        210                 215                 220

Glu Met Gly Tyr Leu Gly Glu Met Ile Ser Asn Thr Pro Phe Phe Phe
225                 230                 235                 240

Tyr Pro Pro Val Lys Pro Thr Gly Lys Val Ala Phe Asp Ile Thr Asn
                245                 250                 255

```
Val Thr Glu Ile Pro Arg Val Asp Ile Leu Phe Ser Tyr Glu Asp Met
            260                 265                 270

His Asn Asp Thr Leu Tyr Asn Ala Ile Ser Ser Gly Ala Gln Gly Ile
        275                 280                 285

Val Ile Ala Gly Val Gly Ala Gly Gly Val Thr Thr Ser Phe Asn Glu
    290                 295                 300

Ala Ile Glu Asp Val Ile Asn Arg Leu Glu Ile Pro Val Val Gln Ser
305                 310                 315                 320

Met Arg Thr Val Asn Gly Glu Val Pro Leu Ser Asp Val Ser Ser Asp
                325                 330                 335

Thr Ala Thr His Ile Ala Ser Gly Tyr Leu Asn Pro Gln Lys Ser Arg
            340                 345                 350

Ile Leu Leu Gly Leu Leu Leu Ser Gln Gly Lys Asn Ile Thr Glu Ile
        355                 360                 365

Ala Asp Val Phe Ala Leu Gly Thr Asp Ala
    370                 375

<210> SEQ ID NO 18
<211> LENGTH: 378
<212> TYPE: PRT
<213> ORGANISM: Artificial Sequence
<220> FEATURE:
<223> OTHER INFORMATION: ASN 15 (mutated from Aspergillus niger)

<400> SEQUENCE: 18

Met Pro Leu Lys Pro Ile Leu Leu Ser Ala Leu Ala Ser Leu Ala Ser
1               5                   10                  15

Ala Ser Pro Leu Leu Tyr Ser Arg Thr Thr Asn Glu Thr Phe Val Phe
            20                  25                  30

Thr Asn Ala Asn Gly Leu Asn Phe Thr Gln Met Asn Thr Thr Leu Pro
        35                  40                  45

Asn Val Thr Ile Phe Ala Thr Gly Gly Thr Ile Ala Gly Ser Asp Ser
    50                  55                  60

Ser Ser Thr Ala Thr Thr Gly Tyr Lys Ala Gly Ala Val Gly Val Leu
65                  70                  75                  80

Ser Leu Ile Asp Ala Val Pro Ser Met Leu Asp Val Ala Asn Val Ala
                85                  90                  95

Gly Val Gln Val Ala Asn Val Gly Ser Glu Asp Ile Thr Ser Asp Ile
            100                 105                 110

Leu Ile Ser Met Ser Lys Lys Leu Asn Arg Val Val Cys Glu Asp Pro
        115                 120                 125

Thr Met Ala Gly Ala Val Ile Thr His Gly Thr Asp Thr Leu Glu Glu
    130                 135                 140

Thr Ala Phe Phe Leu Asp Ala Thr Val Asn Cys Gly Lys Pro Ile Val
145                 150                 155                 160

Ile Val Gly Ala Met Arg Pro Ser Thr Ala Ile Ser Ala Asp Gly Pro
                165                 170                 175

Phe Asn Leu Leu Glu Ala Val Thr Val Ala Ala Ser Thr Ser Ala Arg
            180                 185                 190

Asp Arg Gly Ala Met Val Val Met Asn Asp Arg Ile Ala Ser Ala Tyr
        195                 200                 205

Tyr Val Thr Lys Thr Asn Ala Asn Thr Met Asp Thr Phe Lys Ala Met
    210                 215                 220

Glu Met Gly Tyr Leu Gly Glu Met Ile Ser Asn Thr Pro Phe Phe Phe
225                 230                 235                 240

Tyr Pro Pro Val Lys Pro Thr Gly Lys Val Ala Phe Asp Ile Thr Asn
```

```
            245                 250                 255
Val Thr Glu Ile Pro Arg Val Asp Ile Leu Phe Ser Tyr Glu Asp Met
                260                 265                 270

His Asn Asp Thr Leu Tyr Asn Ala Ile Ser Ser Gly Ala Gln Gly Ile
            275                 280                 285

Val Ile Ala Gly Ser Gly Ala Gly Gly Val Thr Thr Ser Phe Asn Glu
        290                 295                 300

Ala Ile Glu Asp Val Ile Asn Arg Leu Glu Ile Pro Val Val Gln Ser
305                 310                 315                 320

Met Arg Thr Val Asn Gly Glu Val Pro Leu Ser Asp Val Ser Ser Asp
                325                 330                 335

Thr Ala Thr His Ile Ala Ser Gly Tyr Leu Asn Pro Gln Lys Ser Arg
            340                 345                 350

Ile Leu Leu Gly Leu Leu Ser Gln Gly Lys Asn Ile Thr Glu Ile
        355                 360                 365

Ala Asp Val Phe Ala Leu Gly Thr Asp Ala
        370                 375

<210> SEQ ID NO 19
<211> LENGTH: 378
<212> TYPE: PRT
<213> ORGANISM: Artificial Sequence
<220> FEATURE:
<223> OTHER INFORMATION: ASN16 (mutated from Aspergillus niger)

<400> SEQUENCE: 19

Met Pro Leu Lys Pro Ile Leu Leu Ser Ala Leu Ala Ser Leu Ala Ser
1               5                   10                  15

Ala Ser Pro Leu Leu Tyr Ser Arg Thr Thr Asn Glu Thr Phe Val Phe
            20                  25                  30

Thr Asn Ala Asn Gly Leu Asn Phe Thr Gln Met Asn Thr Thr Leu Pro
        35                  40                  45

Asn Val Thr Ile Phe Ala Thr Gly Gly Thr Ile Ala Gly Ser Asp Ser
    50                  55                  60

Ser Ser Thr Ala Thr Thr Gly Tyr Lys Ala Gly Ala Val Gly Val Leu
65                  70                  75                  80

Ser Leu Ile Asp Ala Val Pro Ser Met Leu Asp Val Ala Asn Val Ala
                85                  90                  95

Gly Val Gln Val Ala Asn Val Gly Ser Pro Asp Ile Thr Ser Asp Ile
            100                 105                 110

Leu Ile Ser Met Ser Lys Lys Leu Asn Arg Val Val Cys Glu Asp Pro
        115                 120                 125

Thr Met Ala Gly Ala Val Ile Thr His Gly Thr Asp Thr Leu Glu Glu
    130                 135                 140

Thr Ala Phe Phe Leu Asp Ala Thr Val Asn Cys Gly Lys Pro Ile Val
145                 150                 155                 160

Ile Val Gly Ala Met Arg Pro Ser Thr Ala Ile Ser Ala Asp Gly Pro
                165                 170                 175

Phe Asn Leu Leu Glu Ala Val Thr Val Ala Ala Ser Ser Ala Arg
            180                 185                 190

Asp Arg Gly Ala Met Val Val Met Asn Asp Arg Ile Ala Ser Ala Tyr
        195                 200                 205

Tyr Val Thr Lys Thr Asn Ala Asn Thr Met Asp Thr Phe Lys Ala Met
    210                 215                 220

Glu Met Gly Tyr Leu Gly Glu Met Ile Ser Asn Thr Pro Phe Phe Phe
225                 230                 235                 240
```

```
Tyr Pro Pro Val Lys Pro Thr Gly Lys Val Ala Phe Asp Ile Thr Asn
            245             250             255

Val Thr Glu Ile Pro Arg Val Asp Ile Leu Phe Ser Tyr Glu Asp Met
            260             265             270

His Asn Asp Thr Leu Tyr Asn Ala Ile Ser Ser Gly Ala Gln Gly Ile
            275             280             285

Val Ile Ala Gly Ser Gly Ala Gly Ser Val Ser Thr Ser Phe Asn Glu
            290             295             300

Ala Ile Glu Asp Val Ile Asn Arg Leu Glu Ile Pro Val Val Ala Ser
305             310             315             320

Thr Arg Thr Gly Asn Gly Glu Val Pro Leu Ser Asp Val Ser Ser Asp
            325             330             335

Thr Ala Thr His Ile Ala Ser Gly Tyr Leu Asn Pro Gln Lys Ser Arg
            340             345             350

Ile Leu Leu Gly Leu Leu Leu Ser Gln Gly Lys Asn Ile Thr Glu Ile
            355             360             365

Ala Asp Val Phe Ala Leu Gly Thr Asp Ala
370             375
```